US012207998B2

(12) United States Patent
Denti et al.

(10) Patent No.: US 12,207,998 B2
(45) Date of Patent: Jan. 28, 2025

(54) ABSORBENT ARTICLE HAVING IMPROVED COMFORT

(71) Applicant: The Procter & Gamble Company, Cincinnati, OH (US)

(72) Inventors: Federica Denti, Schwalbach (DE); Alisa Chernenkaya, Friesenheim (DE); Ezgi Keceli, Schwalbach (DE); Gerard A Viens, Wyoming, OH (US); Pietro Cecchetto, Fairfield, OH (US); ImkeAnn Hohn, Schwalbach (DE); Monique Verjans, Steinbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 1235 days.

(21) Appl. No.: 16/832,270

(22) Filed: Mar. 27, 2020

(65) Prior Publication Data

US 2020/0315859 A1 Oct. 8, 2020

Related U.S. Application Data

(60) Provisional application No. 62/829,280, filed on Apr. 4, 2019, provisional application No. 62/946,725, filed on
(Continued)

(51) Int. Cl.
*A61F 13/15* (2006.01)
*A61F 13/47* (2006.01)
(Continued)

(52) U.S. Cl.
CPC ...... *A61F 13/535* (2013.01); *A61F 13/15203* (2013.01); *A61F 13/15747* (2013.01);
(Continued)

(58) Field of Classification Search
CPC .......... A61F 13/15203; A61F 13/511; A61F 13/512; A61F 13/513; A61F 13/51;
(Continued)

(56) References Cited

U.S. PATENT DOCUMENTS 3,156,242 A 11/1964 Crowe, Jr.
3,881,489 A 5/1975 Hartwell
(Continued)

FOREIGN PATENT DOCUMENTS

CN 107106382 A 8/2017
CN 107735065 A 2/2018
(Continued)

OTHER PUBLICATIONS

PCT Search Report and Written Opinion for PCT/US2020/026133 dated Jul. 8, 2020.
(Continued)

*Primary Examiner* — Jessica Arble
(74) *Attorney, Agent, or Firm* — Sarah M. DeCristofaro; Wednesday G. Shipp

(57) ABSTRACT

An absorbent article includes a liquid pervious topsheet, a backsheet at least peripherally joined to the topsheet, and an absorbent core disposed between said topsheet and said backsheet. The absorbent article further includes an integrated nonwoven fluid management layer having a basis weight between about 40 gsm and about 65 gsm; and an Urine Standard Rewet Value of 10 mg or less.

15 Claims, 7 Drawing Sheets

Related U.S. Application Data on Dec. 11, 2019, provisional application No. 62/946,738, filed on Dec. 11, 2019.

(51) Int. Cl.

| | |
|---|---|
| *A61F 13/511* | (2006.01) |
| *A61F 13/512* | (2006.01) |
| *A61F 13/513* | (2006.01) |
| *A61F 13/514* | (2006.01) |
| *A61F 13/53* | (2006.01) |
| *A61F 13/534* | (2006.01) |
| *A61F 13/535* | (2006.01) |
| *A61F 13/537* | (2006.01) |
| *A61F 13/84* | (2006.01) |

(52) U.S. Cl.
CPC .......... *A61F 13/511* (2013.01); *A61F 13/512* (2013.01); *A61F 13/513* (2013.01); *A61F 13/514* (2013.01); *A61F 13/53* (2013.01); *A61F 13/534* (2013.01); *A61F 13/53708* (2013.01); *A61F 13/5376* (2013.01); *A61F 2013/15292* (2013.01); *A61F 2013/15325* (2013.01); *A61F 2013/15357* (2013.01); *A61F 2013/15373* (2013.01); *A61F 2013/15406* (2013.01); *A61F 2013/15422* (2013.01); *A61F 2013/15447* (2013.01); *A61F 2013/15959* (2013.01); *A61F 2013/4708* (2013.01); *A61F 2013/51169* (2013.01); *A61F 2013/51178* (2013.01); *A61F 2013/530233* (2013.01); *A61F 2013/53024* (2013.01); *A61F 2013/530452* (2013.01); *A61F 2013/53062* (2013.01); *A61F 2013/53791* (2013.01); *A61F 2013/8402* (2013.01)

(58) Field of Classification Search
CPC .................. A61F 13/53; A61F 13/5376; A61F 2013/15325; A61F 2013/15406; A61F 2013/4708; A61F 2013/51169; A61F 2013/51178
See application file for complete search history.

(56) References Cited

U.S. PATENT DOCUMENTS

| | | | |
|---|---|---|---|
| 3,989,867 A | 11/1976 | Sisson | |
| 4,216,772 A * | 8/1980 | Tsuchiya | A61F 13/51305 |
| | | | 604/377 |
| 4,341,216 A | 7/1982 | Obenour | |
| 4,591,523 A | 5/1986 | Thompson | |
| 4,695,422 A | 9/1987 | Curro | |
| 4,713,068 A | 12/1987 | Wang | |
| 4,818,600 A | 4/1989 | Braun | |
| 4,839,216 A | 6/1989 | Curro | |
| 5,433,715 A | 7/1995 | Tanzer et al. | |
| 5,458,835 A | 10/1995 | Wilkes | |
| 5,599,335 A | 2/1997 | Goldman et al. | |
| 5,607,414 A | 3/1997 | Richards | |
| 5,634,914 A | 6/1997 | Wilkes | |
| 5,810,796 A | 9/1998 | Kimura | |
| 5,885,265 A | 3/1999 | Osborn, III | |
| 5,997,980 A | 12/1999 | Matoba | |
| 6,060,638 A | 5/2000 | Paul | |
| 6,333,108 B1 | 12/2001 | Wilkes | |
| 6,436,508 B1 | 8/2002 | Ciammaichella | |
| 6,462,251 B1 | 10/2002 | Cimini | |
| 6,547,018 B1 | 4/2003 | Choi | |
| 6,623,464 B2 | 9/2003 | Bewick-sonntag | |
| 6,624,341 B1 | 9/2003 | Depner | |
| 6,642,432 B1 | 11/2003 | Matsui et al. | |
| 6,664,439 B1 | 12/2003 | Arndt | |
| 6,838,154 B1 | 1/2005 | Varona et al. | |
| 6,989,005 B1 | 1/2006 | Lavon et al. | |
| 7,138,561 B2 | 11/2006 | Fuchs | |
| 7,597,689 B2 | 10/2009 | Hoffmann | |
| 7,686,790 B2 | 3/2010 | Rasmussen et al. | |
| 7,750,203 B2 | 7/2010 | Becker | |
| 7,767,598 B2 | 8/2010 | Schneider | |
| 8,389,427 B2 | 3/2013 | Gustafsson | |
| 8,466,336 B2 | 6/2013 | Carlucci | |
| 8,674,169 B2 | 3/2014 | Brennan et al. | |
| 9,295,593 B2 | 3/2016 | Van Malderen | |
| 9,693,910 B2 | 7/2017 | Carlucci | |
| 9,789,009 B2 | 10/2017 | Joseph | |
| 10,307,309 B2 | 6/2019 | Viens | |
| 10,532,123 B2 | 1/2020 | Viens | |
| 10,779,998 B2 | 9/2020 | Miao et al. | |
| 11,285,055 B2 | 3/2022 | Viens et al. | |
| 2001/0027303 A1 | 10/2001 | Bewick-sonntag | |
| 2003/0050615 A1 * | 3/2003 | Sakamoto | A61F 13/5116 |
| | | | 604/367 |
| 2003/0220048 A1 | 11/2003 | Toro | |
| 2004/0018795 A1 | 1/2004 | Viazmensky | |
| 2004/0087924 A1 | 5/2004 | Sroda | |
| 2004/0238393 A1 * | 12/2004 | Ohi | A61F 15/001 |
| | | | 604/385.02 |
| 2005/0015068 A1 | 1/2005 | Bean et al. | |
| 2005/0033253 A1 | 2/2005 | Fuchs | |
| 2005/0136773 A1 | 6/2005 | Yahiaoui | |
| 2006/0058762 A1 | 3/2006 | Yang | |
| 2008/0113574 A1 | 5/2008 | Neron | |
| 2008/0119806 A1 | 5/2008 | Nguyen | |
| 2008/0312622 A1 | 12/2008 | Hundorf | |
| 2011/0060303 A1 | 3/2011 | Bissah et al. | |
| 2011/0282309 A1 | 11/2011 | Adie et al. | |
| 2012/0029460 A1 | 2/2012 | Yamashita et al. | |
| 2012/0041410 A1 | 2/2012 | Ueda | |
| 2012/0209233 A1 | 8/2012 | Steffen et al. | |
| 2012/0238978 A1 | 9/2012 | Weisman et al. | |
| 2014/0005622 A1 | 1/2014 | Wirtz | |
| 2014/0324009 A1 * | 10/2014 | Lee | A61F 13/513 |
| | | | 428/137 |
| 2014/0343523 A1 | 11/2014 | Viens | |
| 2015/0182387 A1 * | 7/2015 | Ferrer | A61F 13/51401 |
| | | | 604/374 |
| 2015/0250654 A1 | 9/2015 | Pernot | |
| 2015/0251976 A1 * | 9/2015 | Chen | C10G 11/00 |
| | | | 252/373 |
| 2015/0351976 A1 * | 12/2015 | Viens | A61F 13/51121 |
| | | | 604/378 |
| 2016/0213532 A1 | 7/2016 | Takahashi | |
| 2017/0119597 A1 | 5/2017 | Bewick-sonntag | |
| 2017/0312148 A1 | 11/2017 | Dobrosielska-oura et al. | |
| 2018/0098889 A1 | 4/2018 | Hardie | |
| 2018/0098893 A1 | 4/2018 | Viens | |
| 2019/0099301 A1 | 4/2019 | Viens et al. | |
| 2019/0247244 A1 | 8/2019 | Viens | |
| 2020/0101191 A1 | 4/2020 | Viens | |
| 2020/0315861 A1 | 10/2020 | Viens | |
| 2020/0315870 A1 | 10/2020 | Viens et al. | |
| 2020/0315871 A1 | 10/2020 | Viens et al. | |
| 2020/0315872 A1 | 10/2020 | Viens et al. | |
| 2020/0315873 A1 | 10/2020 | Viens et al. | |
| 2020/0315874 A1 | 10/2020 | Viens et al. | |
| 2023/0329922 A1 | 10/2023 | Viens et al. | |

FOREIGN PATENT DOCUMENTS

| | | |
|---|---|---|
| EP | 0710472 A1 | 5/1996 |
| EP | 1504739 A1 | 2/2005 |
| EP | 2407133 A1 | 1/2012 |
| EP | 2692321 A1 | 2/2014 |
| EP | 2740454 A1 | 6/2014 |
| JP | H06136650 A | 5/1994 |
| JP | H10273884 A | 10/1998 |
| JP | 2008106383 A | 5/2008 |
| WO | 9110416 A1 | 7/1991 |
| WO | 9723182 A1 | 7/1997 |
| WO | WO97/24097 A1 | 7/1997 |
| WO | 0059431 A1 | 10/2000 |

(56) References Cited

FOREIGN PATENT DOCUMENTS

| WO | 0134085 A1 | 5/2001 |
| WO | 0134215 A2 | 5/2001 |
| WO | 2007014235 A1 | 2/2007 |
| WO | 2008066417 A1 | 6/2008 |
| WO | 2020205946 A1 | 10/2020 |

OTHER PUBLICATIONS

Third Party Observation for PCT/US2020/026133 dated Jul. 30, 2021, 1 page.
All Office Actions; U.S. Appl. No. 16/831,879, filed Mar. 27, 2020.
All Office Actions; U.S. Appl. No. 16/831,865, filed Mar. 27, 2020.
All Office Actions; U.S. Appl. No. 16/831,868, filed Mar. 27, 2020.
All Office Actions; U.S. Appl. No. 16/831,870, filed Mar. 27, 2020.

* cited by examiner

ABSORBENT ARTICLE HAVING IMPROVED COMFORT

FIELD OF THE INVENTION

The present disclosure relates to disposable absorbent articles, more specifically disposable feminine hygiene articles, having fluid management layers.

BACKGROUND OF THE INVENTION

Absorbent sanitary articles are used to collect various bodily fluids for hygiene purposes. For example, pantiliners are normally used by women to receive and contain discharges, including menstrual fluid and urine in the case of incontinence. Consumers often find it desirable to wear absorbent liners for long periods of time and on a daily or otherwise frequent basis. However, prolonged wear can be uncomfortable. Indeed, wearers often find the article fails to stay in the desired position. One or more of the article's edges may deform or bunch, such that the edge or even the panty fastening adhesive becomes exposed to the skin which may cause irritation and/or abrasion. In some instances, the article may deform laterally inward and/or form wrinkles, causing the liner to be positioned uncomfortably in the genital area of the wearer. This bunching effect is especially noticeable for wearers who exert high friction or pressure during wear, such as wearers engaged in sports or wearers having high body-mass index. Further, while consumers typically prefer softer materials in the topsheets, softer materials are often more conformable and thus heighten the undesirable bunching.

Another common failure is the lack of dryness on the wearer-facing topsheet. While absorbent cores are designed to trap and contain fluids, sometimes the core in liners is insufficiently absorbent and/or permits rewetting of the topsheet under compression exerted during wear. Manufacturers have sought to avoid such issues by incorporating impermeable film layers below the topsheet, which may prevent fluids from resurfacing. However, such films may cause the wearer to feel hot and to sweat. On the other hand, softer and/or more breathable materials tend to fail to maintain fluids below the surface.

Therefore, there remains a need to provide an absorbent article with enhanced comfort, through improved resiliency, softness and/or dryness. Further, there is a need to provide an absorbent article that balances the desired characteristics of feel with proper positioning and/or dryness. There is also a need to provide desired properties in a cost efficient and effective manner.

SUMMARY OF THE INVENTION

An absorbent article comprises a liquid pervious topsheet, a backsheet at least peripherally joined to the topsheet, and an absorbent core disposed between the topsheet and the backsheet. The absorbent article also comprises an integrated nonwoven fluid management layer having a basis weight between about 40 gsm and about 65 gsm. The absorbent article exhibits an Urine Standard Rewet of 10 mg or less. The absorbent article may comprise a pantiliner.

A liner comprises a liquid pervious topsheet, a backsheet at least peripherally joined to the topsheet, and an absorbent core disposed between the topsheet and backsheet. The liner further comprises an integrated nonwoven fluid management layer. The liner comprises an increasing porosity gradient in a first z-direction, wherein the first z direction extends from the backsheet towards the topsheet.

A liner comprises a liquid pervious topsheet, a backsheet at least peripherally joined to the topsheet, and an absorbent core disposed between the topsheet and backsheet. The absorbent core comprises an airlaid core with a basis weight of at least 150 gsm. The liner further comprises an integrated nonwoven fluid management layer having a basis weight between about 40 gsm and about 65 gsm. The liner exhibits a Wet CD Bunch Compression of at least about 325 gf.

DETAILED DESCRIPTION OF THE INVENTION

Overview

Figure 1:
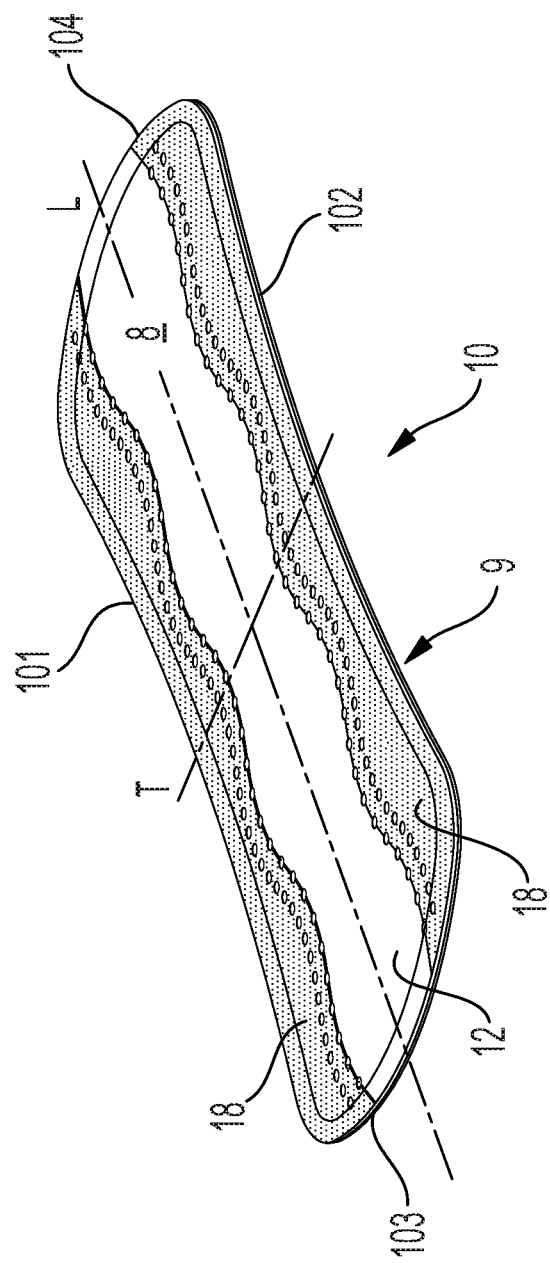
FIG. 1 is a perspective view of a nonlimiting example of an absorbent article in the form of a liner.

As used herein, the following terms shall have the meaning specified thereafter:

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments (e.g., liners, pads and briefs) and/or feminine hygiene articles.

"Design element" as used herein means a shape or combination of shapes that visually create a distinct and discrete form, regardless of the size or orientation of the form. Design elements may comprise objects, character representations, words, colors, shapes or other indicia that can be used to distinguish, identify or represent the manufacturer, retailer, distributor and/or brand of a product, including but not limited to trademarks, logos, emblems, symbols, designs, figures, fonts, lettering, crests or similar identifying marks. Design elements and/or combinations of design elements may comprise letters, words and/or graphics such as flowers, butterflies, hearts, character representations and the like. Design elements and/or combinations of design elements may comprise instructional indicia providing guidance or instruction relative to placement and/or fit of the article about the wearer.

"Feminine hygiene article" refers to disposable absorbent articles to be worn by women for menstrual and/or incontinence control. These articles are commonly referred to as pads, pantiliners/liners, sanitary napkins or sanitary towels. These articles have generally flat surfaces and are typically held in place adjacent the user's crotch (i.e., the pubic region) by the user's undergarment. Feminine hygiene articles can be placed into the user's undergarment and affixed via adhesive or other joining means.

The term "integrated" is used to describe fibers of a nonwoven material which have been intertwined, entangled, and/or pushed/pulled in a positive and/or negative Z-direction (direction of the thickness of the nonwoven material). Some exemplary processes for integrating fibers of a nonwoven web include spunlacing and needlepunching. Spunlacing uses a plurality of high pressure water jets to entangle fibers. Needlepunching involves the use of needles to push and/or pull fibers to entangle them with other fibers in the nonwoven.

The term "macro deformation" refers to structural features or elements that are readily visible and distinctly discernable to a human having 20/20 vision when the perpendicular distance between the viewer's eye and the web is about 12 inches (30 cm). For the sake of clarity, macro deformations specifically exclude embossments. Additional description regarding the difference between macro deformations and embossments is provided herein.

The "longitudinal" direction is a direction running parallel to the maximum linear dimension. "Length" of the article or component thereof, when used herein, generally refers to the size/distance in the longitudinal direction.

The "lateral" or "transverse" direction is orthogonal to the longitudinal direction, i.e. in the same plane of the majority of the article and the longitudinal axis, and the transverse direction is parallel to the transverse axis. "Width" of the article or of a component thereof, when used herein, refers to the size/distance of the dimension orthogonal to the longitudinal direction of the article.

"Film" means a sheet-like material wherein the length and width of the material far exceed the thickness of the material (e.g., 10×, 50×, or even 1000× or more). Films are typically liquid impermeable but may be configured to be breathable.

The "Z-direction" is orthogonal to both the longitudinal and transverse directions.

"Machine Direction" or "MD" as used herein means the direction parallel to the flow of the carded staple-fiber nonwoven through the nonwoven making machine and/or absorbent article product manufacturing equipment.

"Cross Machine Direction" or "CD" as used herein means the direction parallel to the width of the carded staple-fiber nonwoven making machine and/or absorbent article product manufacturing equipment and perpendicular to the machine direction.

As used herein "hydrophilic" and "hydrophobic" have meanings as well established in the art with respect to the contact angle of water on the surface of a material. Thus, a material having a water contact angle of greater than about 90 degrees is considered hydrophobic, and a material having a water contact angle of less than about 90 degrees is considered hydrophilic. Compositions which are hydrophobic, will increase the contact angle of water on the surface of a material while compositions which are hydrophilic will decrease the contact angle of water on the surface of a material. Notwithstanding the foregoing, reference to relative hydrophobicity or hydrophilicity between a material and a composition, between two materials, and/or between two compositions, does not imply that the materials or compositions are hydrophobic or hydrophilic. For example, a composition may be more hydrophobic than a material. In such a case neither the composition nor the material may be hydrophobic; however, the contact angle exhibited by the composition is greater than that of the material. As another example, a composition may be more hydrophilic than a material. In such a case, neither the composition nor the material may be hydrophilic; however, the contact angle exhibited by the composition may be less than that exhibited by the material.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaying, and bonded carded web processes, including carded thermal bonding and carded air-through bonding.

Absorbent Article

FIG. 1 shows the wearer-facing surface 8 of an absorbent article 10 in a typical pantiliner ("liner") configuration. The articles of the invention normally have a generally flat wearer-facing surface but may be curved to conform to the user's body and are generally flexible to adapt to the user's anatomy. The article includes longitudinal sides 101, 102 and lateral ends 103, 104, any of which may be straight or curved.

The dimensions of the articles of the invention are adapted for the use intended as in known in the art. For example, liners are generally smaller and compacter than pads. The thickness of the absorbent articles usually ranges from about 2 mm to about 50 mm. Thin sanitary napkin articles can have a thickness of less than about 6 mm, or even less than about 4 mm.

The length of the article along the longitudinal centerline L of the article may typically be between 10 cm and 25 cm, more typically between 12 cm and 21 cm. The width of the article along the transversal centerline may typically be between 3 and 10 cm, more typically between 4 and 7 cm. Typically the total surface area of the body facing side of a liner is between 50 and 150 cm$^2$, a pad between 60 and 200 cm$^2$ and diapers even larger. A typical surface area for a normal liner may be around 80 cm$^2$. All these dimensions are merely indicative and not limitative, because the normal dimensions of these and other types of absorbent sanitary articles may differ according to the intended use, as is known in the art.

Absorbent hygiene articles are usually substantially symmetrical in relation to the longitudinal centerline, such that the longitudinal centerline divides the article in two substantially symmetrical halves (notwithstanding possible decorations such as embossments or printed patterns). However, although this is preferred, it is not necessary so, for example it has been proposed to use feminine articles with wings which are offset in relation to each other.

Figure 2:
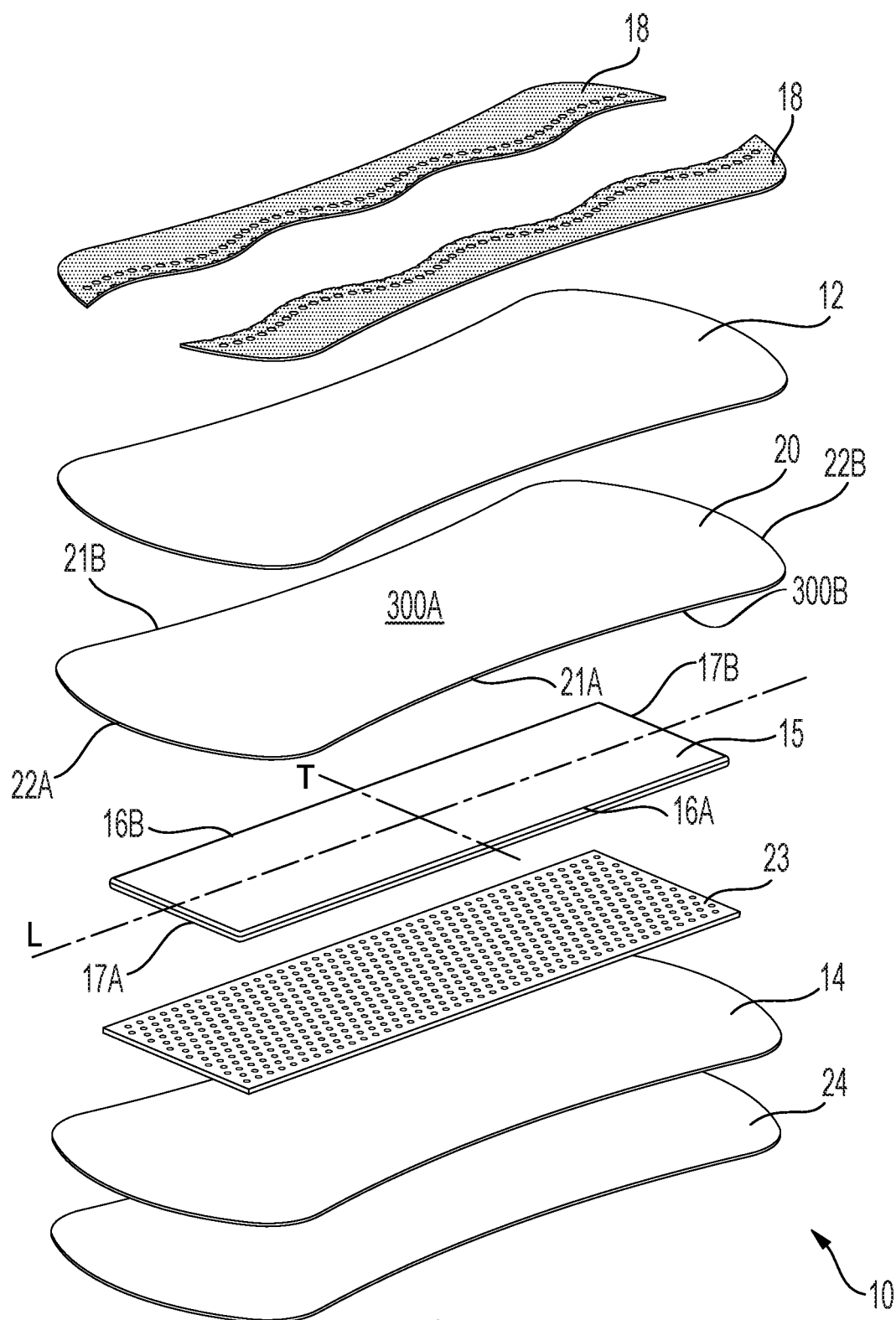
FIG. 2 is an exploded view of the absorbent article of FIG. 1.

FIG. 2 shows the different components or layers of the exemplary embodiment of FIG. 1. The articles of the invention comprise a topsheet 12 forming at least a portion of the wearer-facing surface 8, a backsheet 14 forming at least a portion of the garment-facing side 9, and an absorbent core 15 situated between the topsheet 12 and backsheet 14. Two barrier strips 18 may be disposed on each side of the longitudinal centerline on the wearer-facing side of the topsheet. The barrier strips 18 may comprise nonwoven material, more particularly hydrophobic nonwoven material. In some embodiments, the strips are embossed. The barrier strips 18 may further comprise outboard edges that are coextensive with portions of the periphery of the article. Hydrophobic non-woven material may preferably be inherently hydrophobic without further treatment as will be the case for most plastic materials, for example polyethylene, polypropylene and their mixtures and combinations (as in a "bico", i.e. a bicomponent fiber). A suitable hydrophobic material maybe of the type comprising bicomponent fibers made of polypropylene (PP) as core and polyethylene (PE) as sheath. Such a polymer is for example available from, Pegas a.s (Czech Republic) with a polymer ratio: PP core 70%/PE sheath 30%. This material has a fiber denier (weight of single strand of fiber 9000 meters long) of 2.0 denier and fiber diameter of about 18-20 micron. No additive and/or treatment are required as the polymers (PP, PE) are hydrophobic in nature. Other nonwoven materials which are not inherently hydrophobic may be treated for example by the application of a composition comprising a hydrophobic component. The barrier strips may comprise a basis weight of at least about 10 gsm, or at least about 18 gsm, or from about 10 gsm to about 25 gsm, or from about 15 gsm to about 18 gsm, reciting for each range every 1 gsm increment therein.

The article further includes a fluid management layer 20, and optionally a secondary backsheet 23 and/or a release paper 24.

These and other features are described further below.

Topsheet

The article comprises a topsheet 12 which may be liquid pervious. The topsheet may comprise a nonwoven. The nonwoven may comprise one strata of fibers or may be laminate of multiple nonwoven strata, which may comprise the same or different compositions (e.g., spunbond-meltblown laminate). In various embodiments, the topsheet is a carded, air-through bonded nonwoven. The nonwoven may comprise a mix of hydrophobic and hydrophilic fibers. In some nonlimiting examples, the nonwoven comprises at least about 50%, or at least about 60% hydrophilic fibers by weight of the fibers. Additionally, or alternatively, the nonwoven may comprise at least about 30%, or at least about 40%, or at least about 50% of hydrophobic fibers by weight of the fibers. The nonwoven may comprise a majority of hydrophilic fibers and a minority of hydrophobic fibers. For instance, the nonwoven may comprise about 60% hydrophilic fibers and about 40% hydrophobic fibers. Fibers comprise a size of about 1.2 to about 3.5 denier, or from about 1.3 to about 3 denier, or about 2 denier, reciting for said ranges every 0.1 increment therein. Fibers may be formed from polymeric materials, such as polyethylene (PE) and/or polyethylene terephthalate (PET). Fibers may be in the form of bi-component fibers. In nonlimiting examples, bicomponent fibers which may comprise PET as a core in combination with another polymer as a sheath. In further nonlimiting examples, PE may be used as a sheath in combination with a PET core. Suitable fibers may be staple fibers having a length of at least about 30 mm, or at least about 40 mm, or about at least about 50 mm, or up to about 55 mm, or from about 30 to about 55 mm, or from about 35 to about 52 mm, reciting for said range every 1 mm increment therein. In nonhimiting examples, staple fibers may have a length of about 38 mm.

The topsheet may be apertured. Apertures may comprise a diameter of about 0.5 mm to about 2 mm, reciting for said range every 0.1 mm therein.

The topsheet may comprise a basis weight of at least about 18 gsm, or at least about 22 gsm, or at least about 24 gsm, or up to about 60 gsm, or up to about 50 gsm, or from about 18 gsm to about 60 gsm, reciting for said range every 1 gsm increment therein.

The topsheet may be void of film. Known topsheets for feminine care hygiene products typically include a film, such as hydroformed film, in combination with a nonwoven substrate. The film may prevent liquids from resurfacing and contacting the wearer. The inventors have surprisingly found that a topsheet having the characteristics described herein, particularly in combination with the fluid management layer described below, can effectively prevent rewet to the same degree or better than articles having topsheets comprising film. Without being bound by theory, it is believed that the high basis weight/low density material and macro deformations (discussed below) allow sufficient openness for quick acquisition of fluid while the relative mix of hydrophobic and hydrophilic fibers help lock away liquid insults and thus preventing rewetting. The material of the topsheet is even more efficient in combination with a fluid management layer according to embodiments discussed below.

Figure 3:
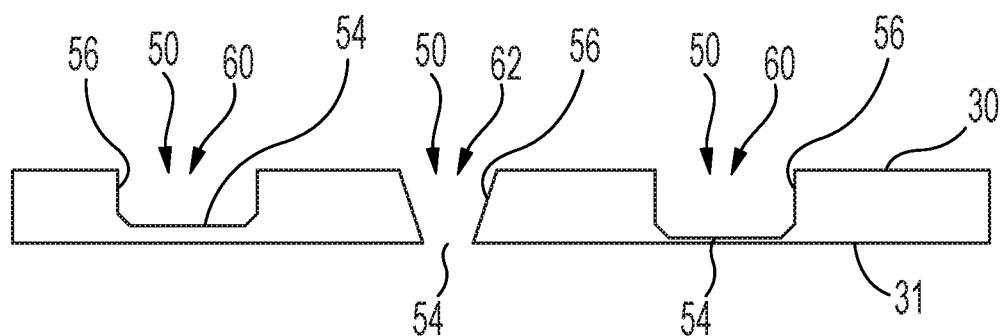
FIG. 3 is a schematic cross sectional representation exemplary macro deformations according to the present disclosure.
Figure 4:
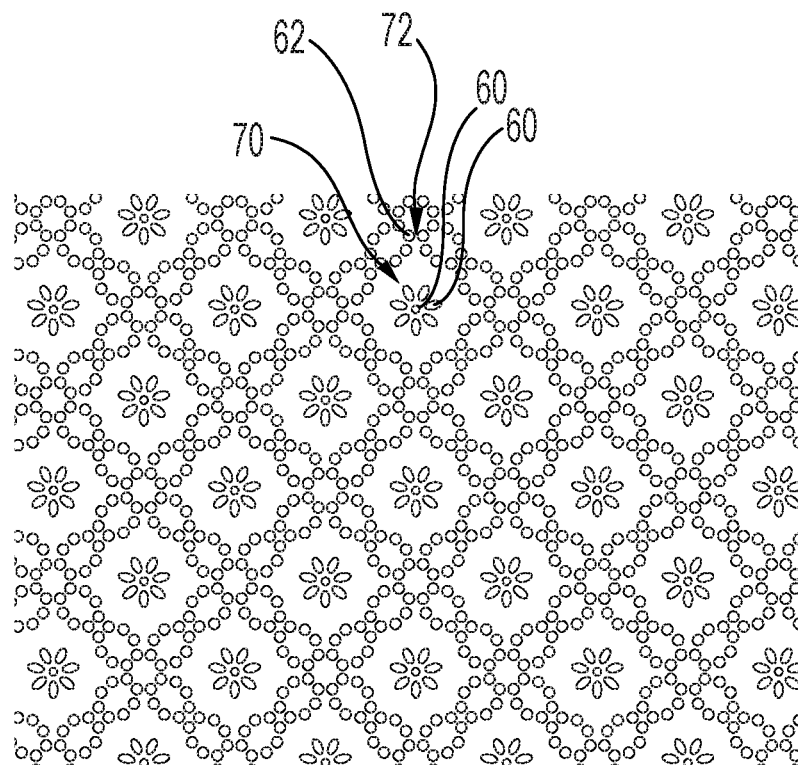
FIG. 4 is a schematic view of an exemplary web having macro-deformations according to the present disclosure.

Turning to FIGS. 3 and 4 the topsheet may comprise a plurality of macro deformations 50 and land areas 52 between adjacent macro deformations 50. Macro deformations 50 are discrete and may be of any suitable configuration. The macro deformations may extend in a negative Z-direction away from a first surface 30 of the topsheet, which may be the wearer-facing surface 8 of the article. Each of the macro deformations 50 comprises a distal end 54 and sidewalls 56 connecting the distal end 54 and the first surface 30. The distal end 54 may be disposed subjacent to a second surface 31 of the topsheet. However, the sidewalls 56 may be configured to extend between the first surface 30 and the second surface 31 of the topsheet.

The distal ends 54 may be closed, thereby forming recessions 60. The distal ends 54 may be open, or the distal ends 54 may be partially open, or combinations thereof. Such open-ended macro deformations 50 may be apertures 62 through one or more layers of the material web. Apertures may comprise a diameter of about 0.5 mm to about 2 mm, reciting for said range every 0.1 mm therein.

Suitable configurations for macro deformations 50 include, but are not limited to, features having plan view configurations including circular, oval, hour-glass shaped, star shaped, diamond, polygonal, the like, and combinations thereof. "Polygonal" herein intends to include polygonal with rounded corners. Polygonal shapes include, but are not limited to triangular, quadrilateral, hexagonal, octagonal or trapezoidal. The macro deformations 50 may be arranged in a staggered pattern. In some forms, the macro deformations 50 have a plan view substantially quadrilateral such as rectangular, square, and lozenge shape. Lozenge shaped macro deformations 50 may be provided in a staggered array as the shapes can be well nested and minimize land area 52 between adjacent macro deformations 50.

The macro deformations 50 may have a major axis and a minor axis perpendicular to the major axis. The major axis of the macro deformations 50 may be substantially parallel to the MD of a material web. The major axis of the macro deformations 50 may be substantially parallel to the CD of the material web. Or, the major axis of the macro deformations 50 may be oriented at an angle relative to the MD of the material web. Despite the terms of "major" and "minor" axes, it is intended that a major axis and a minor axis can have an identical length.

A ratio of the major axis to the minor axis can be about 1:1, greater than about 1.1:1, greater than about 1.2:1, greater than about 1.4:1, specifically including all values within these ranges and any ranges created thereby. The macro deformations may have a major axis that is greater than about 0.5 mm, greater than about 0.8 mm, greater than about 1.0 mm, greater than about 1.2 mm, greater than about 1.5 mm, less than about 2.0 mm, specifically including all values within these ranges and any ranges created thereby. The macro deformations may have a minor axis that is greater than 0.4 mm, greater than 0.5 mm, greater than 0.7 mm, greater than 0.9 mm, greater than 1.0 mm, less than about 1.5 mm, specifically including all values within these ranges and any ranges created thereby.

The plan view area of an individual macro deformations 50, in some forms may be greater than or equal to about 0.25 mm$^2$, 0.5 mm$^2$, 1 mm$^2$, 5 mm$^2$, 10 mm$^2$, or 15 mm$^2$. The number of macro deformations 50 per unit area, i.e., the density of macro deformations 50, can be varied from about 2-60 per/cm$^2$. The material web may comprise macro deformations 50 with a density of from about 2 to about 60, or from about 5 to about 50, or from about 10 to about 40 per/cm$^2$. As an example, there can be at least 30 macro deformations/cm$^2$ of material web in the first zone and/or target area. In general, the macro deformation density need not be uniform across the entire area of the web of the present disclosure, but the macro deformations 50 can be only in certain regions of the web. Additionally, or alternatively, different types of macro deformations may be disposed in different areas of the web.

In some embodiments, a first plurality 70 of macro deformations may be recessions 60 (i.e., formed with closed distal ends) in a first zone. The first plurality may be disposed in a pattern or design element, such as a flower, as show in FIG. 4. The topsheet may further comprise a second plurality of macro deformations 72 in a second zone. One or more of the second plurality may be provided with open ends, such that they are in the form of apertures 62. The first and second zones may be nonoverlapping. The first and second zones may be interspersed as shown in FIG. 4, such that the apertures surround clusters of recessions or a first plurality of macro deformations is intermingled with a second plurality of macro deformations.

Apertures may be disposed throughout the length and/or width of the topsheet to enhance permeability. For instance, lines of apertures may extend throughout the length and/or width of the topsheet. Additionally, or alternatively, recessions 60 may be extend throughout the length and/or width of the topsheet, which may also enhance air permeability. In configurations such as those in FIG. 4, the recessions, which provide soft feel to the wearer, are proximate to apertures, which provide fluid acquisition, and thus the configuration provides a dual benefit that may be localized about a point of fluid insult. Further, where the macro deformations are disposed throughout all or a portion of the topsheet, the dual benefit occurs throughout said portion or the entire topsheet.

Further to the above, without being bound by theory, it is believed that macro deformations on the topsheet reduces the contact points of the topsheet to the wearer's skin and therefore reduces the likelihood that the product will stick to the skin during wear. Given the enhanced permeability and reduced likelihood of contact and sticking, the wearer is provided with a comfortable and airy feeling product.

Macro deformations may be formed by any suitable process. Exemplary processes are disclosed in U.S. patent application Ser. No. 16/547,843. For example, where the distal ends of the macro deformations are open, vacuum-forming, hydro-forming, hot pin aperturing, etc. may be utilized.

It is worth noting that the macro deformations described herein are distinguished from embossments. Embossing involves the compression of a material web between typically two opposing rollers. Generally, one roll comprises male elements which engage a smooth roll. As the web passes between the opposing rollers, the web is compressed between the male elements and the smooth roller.

In contrast, the macro deformations are deformed via stretching rather than compression. Male and female rolls are utilized to stretch a material web (e.g., the precursor material for the topsheet herein). As the material web passes between the male and female rolls, the male elements push the material web into the female elements. This pushing of the material web by the male elements into the female elements stretches the material web at a plurality of discrete locations which correspond to the male elements. In general, the macro deformations of the present disclosure will have a higher air permeability than embossed structures of the same size.

Further to the above, rolls may be provided with forming elements comprising: male elements such as discrete projections such as teeth; female elements such as recesses such as discrete voids in the surface of the rolls; or any suitable combination thereof. The female elements may have a bottom surface (which may be referred to as depressions, or cavities), or they may be in the form of apertures (through holes in the surface of the rolls). In some forms, the forming elements on the members such as the rolls of the forming unit may comprise the same general type (that is, the opposing components may both have male and female elements thereon, or combinations of male and female elements). The forming elements may have any suitable configuration. One type of male elements useful in the formation of macro deformations described herein include teeth having a base in a generally polygonal shape such as octagonal, hexagonal and quadrilateral shape, and having a cross-sectional length and a cross-sectional width. The teeth can have any suitable aspect ratio of its cross-sectional length to its cross-sectional width to form macroscopic structures, in a web. For example, the teeth can have a generally hexagonal shape base or a generally quadrilateral shape base. The male elements can have tips that are flat, rounded or sharp. In general, sharper male elements create apertures in the macro deformation distal ends. A lower depth of engagement can minimize the stretching of the distal ends of the macro deformations which can create a closed or less open distal end. Additionally, rounded or sharper male elements can help to displace filaments/fibers from the distal ends of the macro deformations which is believed to benefit fluid acquisition.

In certain forms, the shapes of the female elements may differ from the shapes of any mating male elements. In some forms, the female elements can be configured to mate with one or more male elements.

During formation of the macro deformations, the material web may be stabilized by heat-setting. The heat-set may be conducted by resting over the material web on male elements of heated roll at or near the softening point of the web material. The heat-set temperature is preferably in the range of ±5° C. of a softening point temperature of the nonwoven material; for nonwovens with biocomponent fibers, the heat-set temperature is preamble in the range of ±5° C. of a softening point temperature of the sheath material. Additionally, or alternatively, the roll with female elements may be heated. The rolls may be heated by means known in the art such as by incorporating hot oil filled rolls or electrically-heated rolls. Alternatively, both or either of the rolls may be heated by surface convection or by surface radiation.

The term "softening point temperature", as used herein, represents a material temperature that is between 70% and 99% of the melt point of the material (i.e., the sheath of bicomponent fiber materials). For example, if a material, regardless of whether it is an alloy, a composite, or a pure element, has a stated melt point of 100 degrees Celsius, then the softening point temperature of the material is 70 degrees Celsius to 99 degrees Celsius.

In certain embodiments, bicomponent fibers formed from PE (sheath)/PET (core) or partially formed from PET are preferable because the PET polymer does not have good recovery properties, and thereby easily forms macro deformations. Notwithstanding its ability to easily conform, the polymer produces resilient fibers, which maintain their shape under compression during wear.

Rolls can be created where the zones comprise a mixture of male and female elements. For example, a first zone of a first roll may be configured with both male and female elements which engage with corresponding female and male elements of a first zone on a second roll. The second zones and third zones may be similarly configured. This configuration of the rolls can provide, for example, a target zone for fluid acquisition in and another target zone for better feel (e.g., a soft-cushiony feel).

In some embodiments, the topsheet may also be embossed.

Fluid Management Layer

A fluid management layer is disposed between the absorbent core and the topsheet. Returning to FIG. 2, the fluid management layer 20 comprises opposing end edges 22A and 22B which may extend generally parallel to a transverse axis T and may be straight or curved. And, the fluid management layer 20 comprises side edges 21A and 21B which may extend generally parallel to the longitudinal axis L and may be straight or curved. The fluid management layer of the present disclosure comprises a plurality of carded, integrated fibers. The fluid management layer provides increased caliper to the absorbent article which can translate into a softer feeling article. Additionally, the fluid management layer of the present disclosure can provide increased resiliency to the absorbent article over that of currently available absorbent articles. Typically, there is a tradeoff with resiliency and softness. Softer materials may have difficulty recovering their shape from insults of force in one or more directions. And the converse may be true for resilient materials. In the absorbent article context, resilient materials typically exhibit good recovery from insults of force; however, they are typically not perceived as being very soft. It is also worth noting that many absorbent articles can exhibit good resilience properties when dry; however, upon absorption of a liquid insult, their resiliency decreases substantially. The absorbent articles of the present disclosure exhibit good resiliency properties both in dry and wet conditions.

In addition to the softness and resiliency benefits, fluid acquisition and low rewet are additional benefits of absorbent articles of the present invention. Regarding fluid acquisition speed, this attribute is key in making the user feel dry and clean. When the absorbent article takes a long time to drain liquid insults from the topsheet, users can feel wet. Additionally, when fluid stay on the topsheet for an extended period of time, users can feel like their skin in the intimate area is unclean. Further, in contrast to some menstrual pads, liners are often worn for long periods of time; and thus, there is a risk that compression during wear will draw fluids back to the surface at some point. In which case, the wearer will feel wet and sense failure in the product. The absorbent article of the present invention mitigates rewet due to its open structure to quickly desorb fluid from upper layers to the core and high z-direction resiliency to prevent fluids from resurfacing.

As noted previously, the fluid management layer is an integrated, carded, nonwoven material. The fluid management layer of the present disclosure may comprise one or more carded webs which are subsequently fiber integrated with one another. Where only one carded web is utilized, the fibers of the carded web are integrated.

A wide variety of configurations for a fluid management layer may be achieved. However, it is important that the fluid management layer of the present disclosure have adequate openness to allow for quick acquisition of fluid. With this in mind, the carded webs which make up the fluid management layer may be different from one another. For example, one of the carded webs may comprise a different fiber blend than the others. Specifically, assuming the first carded web would be closest to the wearer-facing surface in an absorbent article, the fiber selection for a first carded web may be such that there is more openness associated with this web. A second carded web may be similarly configured. In contrast, a third carded web may be configured to collect liquid insults from the void space of the first and second carded webs and effectively distribute these liquid insults to an absorbent core (heterogeneous configuration). Alternatively, the first carded web, the second carded web and the third carded web may be configured the same (homogeneous configuration).

Once the carded web(s) are integrated, they cannot be manually separated—at least not without substantial effort and time. Each carded nonwoven web forms a stratum in the overall fluid management layer. Each stratum can maintain its unique properties for at least a portion of the stratum along the z-direction, even when integrated into a larger fluid management layer. The fluid management layer can provide capillary suction to "pull" fluid through the topsheet, which is competing for trickle/low flow conditions. The fluid management layer also can contain a gush by providing distribution functions to efficiently utilize the absorbent core, as well as provide intermediate storage until the absorbent core can accept fluid.

As noted previously, absorbent articles which exhibit a soft cushiony feel, good resiliency and fluid handling characteristics is in accordance with the present disclosure. The caliper of the fluid management layer therein is important. Notably, typical calipers of webs from conventional spunlace lines achieve a caliper factor (caliper per 10 gsm of basis weight) of 0.03 to 0.10. In contrast, the fluid management layers of the present disclosure can exhibit a caliper factor of at least 0.12 mm, more preferably at least about 0.17 mm, or most preferably about 0.2 mm, including any values within these ranges and any ranges created thereby. The fluid management layer of the present disclosure can have a caliper factor of between 0.12 mm to about 0.3 mm, or more preferably from about 0.13 mm to about 0.25 mm, or most preferably from about 0.15 mm to about 0.22 mm, including all values within these ranges and any ranges created thereby. The caliper and caliper factor of the fluid management layers of the present disclosure may be determined by the Caliper and Caliper Factor test methods disclosed herein.

The inventors have surprisingly discovered that in order to achieve the increase in caliper factor, a simpler process path may be utilized to produce the spunlace web. Generally, the web path through a hydroentangling line is tortuous and subjects the web to both compressive and tensile stresses. This tortuous web path requires water jet pressures high enough to entangle the fibers, creating tensile strength sufficient to survive subsequent web handling. These water jets are applied to both surfaces of the web. This additional water pressure required to create sufficient entanglement for tensile strength is generally in excess of the pressure needed to create the desired fluid handling pore structure and meaningfully reduces caliper of the resultant web. Additionally, the web is subject to significant radial compression and tensile stress as the web is wound around a variety of vacuum drums and rolls such that additional water jets can further entangle the constituent fibers of the strata. Moreover, these webs may be subsequently wound around dryer drums subjecting them to additional compressive force. However, the inventors have found that winding of the web around these rolls causes compression on the web and actually reduces the caliper of the web.

In contrast, the inventors have discovered that through the use of a simplified web path that reduces radial compressive stresses/excessive tensile forces and the appropriate selection of fibers in the fluid management layer, caliper of the fluid management layers of the present disclosure can be maintained. For example, the use of rolls and the number of water jets utilized can be reduced via the simplified path. As such, while the level of entanglement is not to the extent provided by the conventional process, sufficient tensile strength in the web can be provided by selecting the appropriate combination of fibers as disclosed herein, e.g. stiffening fibers which can be heat treated. Again, the simplified path and appropriate fiber selection as described herein, allows the fluid management layers of the present disclosure to achieve caliper factors that have heretofore not been achievable.

Additionally, the caliper factors of the fluid management layers of the present disclosure mentioned above were derived from caliper data from material which was rolled for storage/shipping. Caliper measures pre-winding could be taken which would yield much higher caliper factors. However, such caliper measurements may not necessarily reflect the fluid management layer that makes it into an article.

The fluid management layer may have a basis weight of between about 20 gsm to 80 gsm, or more preferably between 35 gsm to about 75 gsm, or most preferably from about 40 gsm to about 65 gsm, or from about 45 gsm to about 60 gsm, specifically including all values within these ranges and any ranges created thereby. In one specific example, the fluid management layer of the present disclosure can have a basis weight of between about 45 gsm to about 55 gsm. The basis weights of the fluid management layers of the present disclosure may be determined by the Basis Weight method disclosed herein.

The inventors have also found that the processing technique for creating caliper in the fluid management layer can be utilized not only on spunlace materials where the strata are heterogeneous but also where the strata are homogeneous, e.g. each stratum has the same fiber makeup. Additionally, the inventors have surprisingly found that spunlace materials constructed with this process along with appropriate fiber selection can also provide good resiliency and recovery from compression, with improved fluid handling performance above those spunlace materials that are produced via typical spunlace processes.

It is also worth noting that due to the fiber integration, the fluid management layer does not require adhesives or latex binders for stability. Additionally, the carded staple-fiber nonwoven of the fluid management layer can be manufactured from an assortment of suitable fiber types that produce the desired performance characteristics. For example, the fluid management layer may comprise a combination of stiffening fibers, absorbent fibers and resilient fibers.

As will be discussed in additional detail hereafter, the types of fibers in the fluid management layer of the present disclosure are described in terms of their functionality within the fluid management layer. For example, absorbent fibers are utilized to absorb liquid insults. Stiffening fibers are utilized to bond together via heat treatment thereby providing stiffness and resiliency to the fluid management layer. Resilient fibers are utilized to provide recovery from compressive forces which act against the fluid management layer.

In order to enhance the stabilizing effect of the integration, crimped, carded fibers may be utilized. One or more of the absorbent fibers, stiffening fibers, and resilient fibers may be crimped prior to integration. For example, where synthetic fibers are utilized, these fibers may be mechanically crimped via intermeshing teeth. As for the absorbent fibers, these fibers may be mechanically crimped and/or may have a chemically induced crimp due to the variable skin thickness formed during creation of the absorbent fibers.

As noted previously, the amount of absorbent fibers can impact the absorption of liquid insults to the wearer-facing surface or topsheet. However, when absorbent fibers absorb liquid, they tend to lose some of their structural integrity. The loss of structural integrity can reduce the resiliency of the absorbent article and lead to increased bunching and increased leakage. Accordingly, while in principle, a large percentage of absorbent fibers is good for draining liquid insults from the wearer-facing surface and/or topsheet rapidly, a large percentage can also lead to other problems with the absorbent article as mentioned heretofore.

In light of the potential problems associated with having too much of a weight percentage of absorbent fibers, the inventors have found that the fluid management layer of the present disclosure may comprise preferably from about 10 percent to about 60 percent by weight, more preferably from about from about 15 percent to about 50 percent by weight, most preferably from about 20 percent to about 40 percent by weight, specifically including any values within these ranges and any ranges created thereby of absorbent fibers. In one specific example, the fluid management layer may comprise about 30 percent by weight of absorbent fibers. In yet another specific example, the fluid management layer may comprise about 20 percent absorbent fibers. The weight percentages of the absorbent fibers, resilient fibers, and/or stiffening fibers may be determined via the Material Compositional Analysis method disclosed herein.

Additionally, due to the loss of integrity of the absorbent fibers when wet, the fluid management layer also should comprise sufficient weight percentage of resilient fibers which impact the recovery of the absorbent article from compressive loads experienced during use. The inventors have found that the fluid management layer of the present disclosure may comprise from about 15 percent to about 70 percent, more preferably from about 20 percent to about 60 percent, or most preferably from about 25 percent to about 50 percent by weight of resilient fibers, specifically reciting all values within these ranges and any ranges created thereby. In one specific example, the fluid management layer may comprise about 40 percent by weight resilient fibers. In another specific example, the fluid management layer may comprise about 30 percent by weight of resilient fibers.

Moreover, stiffening fibers may be utilized to help the fluid management layer of the present disclosure provide resiliency to the absorbent article. For example, as discussed hereafter, stiffening fibers may be bonded to one another via heat treatment of the fluid management layer during production. This bonding of the stiffening fibers creates a support matrix which helps with resiliency and stiffness of the fluid management layer. With this in mind, the fluid management layer may comprise from about 25 percent to about 70 percent, more preferably from about 30 percent to about 60 percent, or most preferably from about 40 percent to about 55 percent of stiffening fiber, specifically reciting all values within these ranges and any ranges created thereby. In one specific example, the fluid management layer may comprise about 50 percent by weight of stiffening fibers.

As mentioned previously, the fluid management layers of the present disclosure can provide their respective absorbent articles with a soft cushiony feel with good resiliency. Where caliper, resiliency, and a soft cushiony feel are the objective, the weight percentage of stiffening fibers may be greater than or equal to the weight percentage of resilient fibers. The weight percentage of absorbent fibers should be less than the weight percentage of resilient fibers and/or stiffening fibers. In general, a higher weight percentage of absorbent fibers is considered to be beneficial in rapidly absorbent fluid insults; however, given the proximity of the absorbing fibers to the topsheet, it is beneficial for the absorbent core to dewater the absorbing fibers. Where there is a larger percentage of absorbing fibers, typically a larger core is required to dewater the absorbent fibers. This typically leads to higher costs. With this in mind, a ratio of absorbent fibers in the fluid management layers of the present disclosure to stiffening fibers by weight percentage can be from about 1:7 to about 2:1, more preferably from about 1:4 to about 1.5:1, most preferably from about 1:2 to about 1:1, specifically reciting all values within these ranges and any ranges created thereby Similarly a ratio of absorbent fibers to resilient fibers by weight percentage can be from about 1:7 to about 3:1, more preferably from about 1:2 to about 2:1, or most preferably from about 1:1.5 to about 1:1, specifically reciting all values within these ranges and any ranges created thereby.

Regardless of whether the fluid management layer is utilized in an adult incontinence article menstrual article, liner, or other hygiene article, of importance is the ability of the fluid management layer to acquire liquid insults from the topsheet and to pull the liquid far enough from the topsheet, such that the topsheet does not feel wet. To accomplish this, the inventors have found that the increased caliper of the fluid management layer discussed herein can facilitate fluid acquisition due to the increased void volume of the fluid management layer. The higher caliper at the lower basis weight equals more void volume with higher permeability.

It is worth noting that for a set basis weight of a fiber, larger diameter fibers can provide more void volume between adjacent fibers as compared to their smaller diameter counterparts. As such, the fiber size of the fibers in the fluid management layer can be important. For example, for a set percentage weight of fiber, as fiber size goes up there are fewer fibers per gram, and fewer fibers can equal more space between the fibers. Ideally, particularly in the context of menstrual fluid, the fluid management layer should have void volume as well as some degree of capillarity to drain the topsheet.

With the above in mind, the inventors have also surprisingly discovered that careful selection of the fiber types in each of the strata in the fluid management layer and the linear densities of the fiber types can achieve the desired outcome of quick acquisition and low rewet. The fiber types of the individual strata are discussed in additional detail hereafter. It is worth noting that the discussion below regarding fiber types in the strata of the fluid management layer assumes that the first carded nonwoven web is nearer to the topsheet than the web(s) of the additional card(s).

Some suitable linear density values of absorbent fibers for use in the fluid management layers of the present disclosure are provided. For example, the absorbent fiber linear density may range from about 1 dtex to about 7 dtex, more preferably from about 1.4 dtex to about 6 dtex, or most preferably from about 1.7 dtex to about 5 dtex, specifically reciting all values within these ranges and any ranges created thereby. In one specific example, the absorbent fiber may comprise a linear density of about 1.7 dtex. The dtex of the absorbent fibers, stiffening fibers, and resilient fibers may be determined via the Fiber Decitex method disclosed herein.

The absorbent fibers of the fluid management layer may have any suitable shape. Some examples include trilobal, "H," "Y," "X," "T," round, or flat ribbon. Further, the absorbing fibers can be solid, hollow or multi-hollow. Other examples of suitable multi-lobed, absorbent fibers for utilization in the fluid management layers detailed herein are disclosed in U.S. Pat. No. 6,333,108 to Wilkes et al, U.S. Pat. No. 5,634,914 to Wilkes et al., and U.S. Pat. No. 5,458,835 to Wilkes et al. The trilobal shape can improve wicking and improve masking. Suitable trilobal rayon is available from Kelheim Fibres and sold under the trade name Galaxy. While each stratum may comprise a different shape of absorbing fiber, much like mentioned above, not all carding equipment may be suited to handle such variation between/among strata. In one specific example, the fluid management layer comprises round absorbent fibers.

Any suitable absorbent material for the absorbent fibers may be utilized. Some examples of absorbent materials include cotton, pulp, rayon or regenerated cellulose or combinations thereof. In one example, the fluid management layer 20 may comprise viscose cellulose fibers. The length of the absorbent fibers can be in the range of about 20 mm to about 100 mm, or more preferably about 30 mm to about 50 mm or most preferably about 35 mm to about 45 mm, specifically reciting all values within these ranges and any ranges created thereby. In general, the fiber length of pulp is from about 4 to 6 mm and cannot used in conventional carding machines because the pulp fibers are too short. So, if pulp is desired as a fiber in the fluid management layer, then additional processing to add pulp to the carded webs may be required. As an example, pulp may be airlaid between carded webs with the combination being subsequently integrated. As another example, tissue may be utilized in combination with the carded webs and the combination may be subsequently integrated.

As noted previously, in addition to absorbent fibers, the fluid management layer of the present disclosure may comprise stiffening fibers. Stiffening fibers may be utilized to help provide structural integrity to the fluid management layer. The stiffening fibers can help increase structural integrity of the fluid management layer in a machine direction and/or in a cross-machine direction which can facilitate web manipulation during processing of the fluid management layer for incorporation into a disposable absorbent article.

Some suitable linear density values of stiffening fiber are provided. For example, the stiffening fiber linear density may range from about 1.0 dtex to about 6 dtex, more preferably from about 1.5 dtex to about 5 dtex, or most preferably from about 2.0 dtex to about 4 dtex, specifically reciting all values within these ranges and any ranges created thereby. In another specific example, the dtex of the stiffening fibers is about 2.2 dtex.

Some examples of suitable stiffening fibers include bi-component fibers comprising polyethylene and polyethylene terephthalate components or polyethylene terephthalate and co-polyethylene terephthalate components. The components of the bi-component fiber may be arranged in a core sheath arrangement, a side by side arrangement, an eccentric core sheath arrangement, a trilobal arrangement, or the like. In one specific example, the stiffening fibers may comprise bi-component fibers having polyethylene/polyethylene terephthalate components arranged in a concentric, core—sheath arrangement where the polyethylene is the sheath.

While other materials may be useful, the inventors have found that the stiffness of polyethylene terephthalate is useful in creating a resilient structure. In contrast, the polyethylene component of the stiffening fibers can be utilized to bond to one another during heat treatment. This can help provide tensile strength to the web in both the MD and CD. Additionally, the bonding of the polyethylene component to other polyethylene components of stiffening fibers can create fixed points in the nonwoven. These fixed points can reduce the amount of fiber-to-fiber sliding which can increase the resiliency of the material.

One of the benefits of the stiffening fibers is that the integrated nonwoven may be heat treated post fiber entanglement. The heat treatment can provide additional structural integrity to the integrated nonwoven by forming bonds between adjacent stiffening fibers. So, where there is a higher percentage of stiffening fibers, more connection points may be created. Too many connection points can yield a much stiffer fluid management layer which may negatively impact comfort/softness. As such, the weight percentage of the stiffening fibers is of critical importance when designing an absorbent article.

Regarding the heat stiffening process, any suitable temperature may be utilized. And, the suitable temperature may be impacted, in part, by the constituent chemistry of the stiffening fibers as well as by the processing fluid management layer web. For example, the fluid management layer web may be heat stiffened at a temperature of about 132 degrees Celsius. However, it is also worth noting, that in order to provide a uniform stiffness property across the fluid management layer, any heating operation should be set up to provide uniform heating to the fluid management layer web. Even small variations in temperature can greatly impact the tensile strength of the fluid management layer.

As noted previously, the fluid management layer of the present disclosure comprises resilient fibers. The resilient fibers can help the fluid management layer maintain its permeability and compression recovery. Any suitable size fiber may be utilized. For example, the resilient fibers can have a linear density of about 4 dtex to about 15 dtex, more preferably from about 5 dtex to about 12 dtex, or most preferably from about 6 dtex to about 10 dtex, specifically reciting all values within these ranges and any ranges created thereby. In one specific example, the fluid management layer may comprise resilient fibers having variable cross sections, e.g. round and hollow spiral, and/or may comprise resilient fibers having variable dtex's. In yet another specific example, the resilient fibers of the present disclosure may comprise a dtex of about 10. In such forms, the resilient fibers may be hollow spiral.

The resilient fibers can be any suitable thermoplastic fiber, such as polypropylene (PP), polyethylene terephthalate, or other suitable thermoplastic fibers known in the art. The length of the resilient fibers can be in the range of about 20 mm to about 100 mm, or more preferably about 30 mm to about 50 mm or most preferably about 35 mm to about 45 mm. The thermoplastic fibers can have any suitable structure or shape. For example, the thermoplastic fibers can be round or have other shapes, such as spiral, scalloped oval, trilobal, scalloped ribbon, and so forth. Further, the PP fibers can be solid, hollow or multi-hollow. The resilient fibers may be solid and round in shape. Other suitable examples of resilient fibers include polyester/co-extruded polyester fibers. Additionally, other suitable examples of resilient fibers include bi-component fibers such as polyethylene/polypropylene, polyethylene/polyethylene terephthalate, polypropylene/polyethylene terephthalate. These bi-component fibers may be configured as a sheath and a core. The bi-component fibers may provide a cost-effective way to increase basis weight of the material while additionally enabling optimization of the pore size distribution.

The resilient fibers can be polyethylene terephthalate (PET) fibers, or other suitable non-cellulosic fibers known in the art. The PET fibers can have any suitable structure or shape. For example, the PET fibers can be round or have other shapes, such as spiral, scalloped oval, trilobal, scalloped ribbon, hollow spiral, and so forth. Further, the PET fibers can be solid, hollow or multi-hollow. In one particular example, fibers may be fibers made of hollow/spiral PET. Optionally, the resilient fibers may be spiral-crimped or flat-crimped. The resilient fibers may have a crimp value of between about 4 and about 12 crimps per inch (cpi), or between about 4 and about 8 cpi, or between about 5 and about 7 cpi, or between about 9 and about 10 cpi. Particular non-limiting examples of resilient fibers can be obtained from Wellman, Inc. Ireland under the trade names H1311 and T5974. Other examples of suitable resilient fibers for utilization in the carded staple-fiber nonwovens detailed herein are disclosed in U.S. Pat. No. 7,767,598 to Schneider et al.

It is worth noting that the stiffening fibers and resilient fibers should be carefully selected. For example, while the constituent chemistries of the stiffening fibers and the resilient fibers may be similar, resilient fibers should be selected such that their constituent material's melting temperature is higher than that of the stiffening fibers. Otherwise, during heat treatment, resilient fibers could bond to stiffening fibers and vice versa and could create an overly rigid structure.

Without wishing to be bound by theory, it is believed that for weight percentage of absorbent fibers above about 30 percent, within the gsm ranges disclosed herein, the resilient fibers and/or stiffening fibers should be carefully selected. Where a soft, cushiony fluid management layer with a caliper factor of at least 0.12 or greater as described herein, the resilient and/or stiffening fibers should be selected to counteract the loss of structural integrity of the absorbent fibers. For example, a higher dtex of resilient fiber may be beneficial in counteracting the loss of integrity experienced by the absorbent fibers. In such instances, resilient fibers may be utilized having a dtex of between about 5 dtex to about 15 dtex, more preferably from about 6 dtex to about 12 dtex, or most preferably from about 7 dtex to about 10 dtex.

In addition to or an alternative thereof, the stiffening fibers may be configured to provide greater structural integrity. For example, the stiffening fibers may comprise bicomponent fibers in a core-sheath configuration where the sheath is co-polyethylene terephthalate. However, with such a material change, additional problems may occur. For example, the joining of materials to the fluid management layer may then only be via adhesive as opposed to fusion bonding.

Still another example which is in addition to or independent of the foregoing is an increase in bonding of the stiffening fibers. Where the absorbent fibers comprise more than 30 percent by weight of the fluid management layer, the heat at which the stiffening fibers are bonded may be increased and/or the time of exposure may be increased. This should increase the number of bonds in the stiffening fiber matrix which should counteract the loss of integrity of the absorbent fibers when wet. However, with the increase in the number of bonds comes an increase in stiffness. The increase in stiffness can decrease the perception of softness by the user. In a similar regard, in addition to or alternatively thereto, the linear density of the stiffening fibers may be increased to combat the loss of integrity of the absorbent fibers, where the absorbent fibers make up 30 percent by weight or more. In such instances, the linear density of the stiffening fibers may be from about 3 dtex to about 6 dtex, more preferably from about 4 dtex to about 6 dtex.

It is worth noting that while it may appear that the solution to wet collapse is simply to use larger dtex fibers, their use must be balanced. Particularly for viscous fluids, the fluid management layer of the present disclosure should have some degree of capillarity to help drain liquid insults to the wearer-facing surface of the article. Unfortunately, while the use of large dtex fibers can provide caliper benefits, it also detracts from capillarity.

A schematic representation of an exemplary fluid management layer in accordance with the present disclosure is provided in FIG. 2. As shown, the fluid management layer 20 comprises the first surface 300A and the opposing second surface 300B. Between the first surface 300A and the second surface 300B, the fluid distribution layer 20 comprises two or more strata along the Z-direction.

Figure 5:
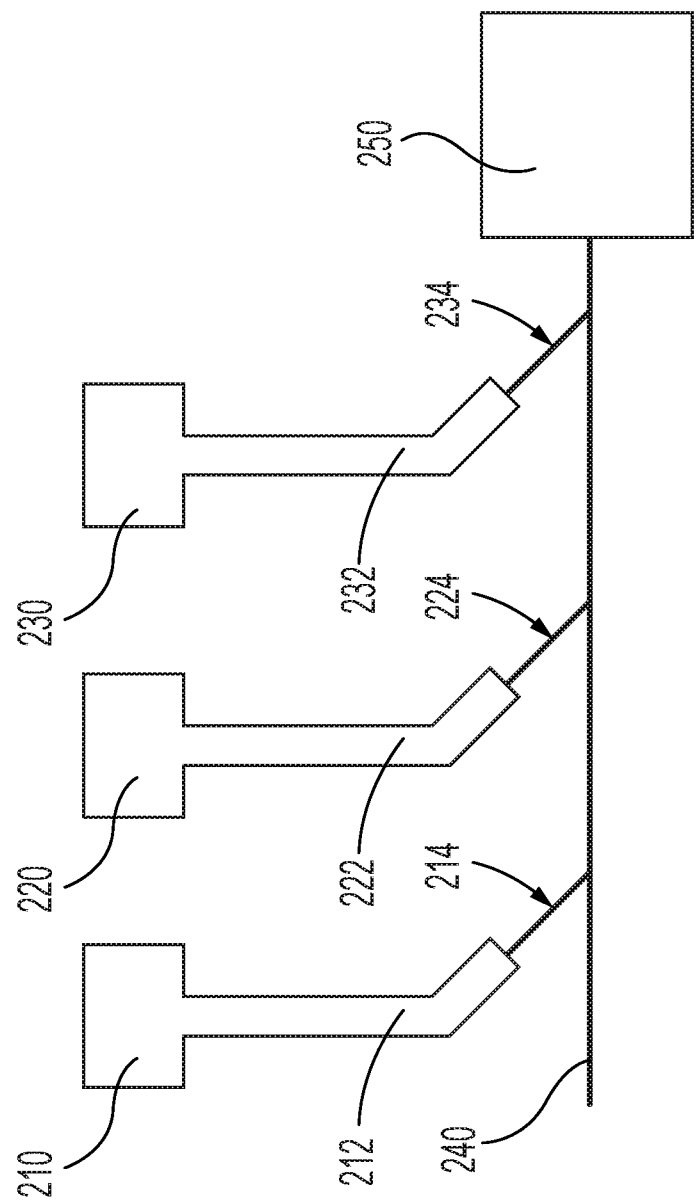
FIG. 5 is a schematic representation of a process which can be utilized to construct fluid management layer of the present disclosure.

The fluid management layer may be formed of one or more nonwoven webs. An exemplary process for forming the fluid management layer of the present disclosure is shown in FIG. 5. As shown, a plurality of carding machines 210, 220, and 230 may each create a carded nonwoven web, e.g. 214, 224, and 234, respectively, which is transferred to a carrier belt 240. Each of the carded nonwoven webs 214, 224, and 234, may be provided to the carrier belt 240 via a web chute 212, 222, 232, respectively. It is also worth noting that after the carded nonwoven 214 is deposited on the carrier belt 240, the carded nonwoven 224 is then deposited on the first carded nonwoven 214 on the carrier belt 240. Similarly, the third carded nonwoven web 234 deposited on the second carded nonwoven 224 and the first carded nonwoven 214 on the carrier belt 240. Subsequently, each of the first, second, and third carded nonwoven webs 214, 224, and 234 are then provided to an integration process 250 which utilizes either needles and/or high-pressure water streams to entangle the fibers of the first, second, and third carded nonwoven webs. Both carding and integration processes are well known in the art.

Additional carding machines may be utilized. Or alternatively, the first carded nonwoven web may be re-looped under the carding machine to create an additional stratum on the first carded nonwoven web. The same may be done to the second carded nonwoven web. The resultant structure would be a nonwoven web with four strata. Additionally, the fluid management layer of the present disclosure may be produced utilizing only two out of the three cards. In such instances, the first carded web 214 would be deposited on the carrier belt 240. And, subsequently, the second carded web 224 would be deposited on the first carded web 214. Then, the first carded web 214 and the second carded web 224 would be integrated as described herein.

It is worth noting that with the arrangement provided in schematic diagram of FIG. 5, a wide variety of configurations for a fluid management layer may be achieved. However, it is important that the fluid management layer of the present disclosure have adequate openness to allow for quick acquisition of fluid yet also are able to lock away liquid insults to reduce the likelihood of rewet. With this in mind, where more than one carded web is used, the carded webs, i.e. 214, 224, and/or 234, may be different from one another. For example, one of the carded webs may comprise a different fiber blend than the others. Specifically, assuming the first carded web would be closest to the wearer-facing surface in an absorbent article, the fiber selection for the first carded web 214 may be such that there is more openness associated with this web. The second carded web 224 may be similarly configured. In contrast, the third carded web 234 may be configured collect liquid insults from the void space of the first and second carded webs 214 and 224 and effectively distribute these liquid insults to an absorbent core. Alternatively, the first carded web 214, the second carded web 224 and the third carded web 234 may be configured the same.

Absorbent Core

The article further comprises an absorbent core 15, which serves as a storage layer for bodily exudates. The configuration and construction of the absorbent core 15 may vary (e.g., the absorbent core 15 may have varying caliper zones, a hydrophilic gradient, a superabsorbent gradient, or lower average density and lower average basis weight acquisition zones). The absorbent core 15 comprises opposing end edges 17A and 17B which may extend generally parallel to the transverse axis T and may be straight or curved. And, the absorbent core 15 may comprise side edges 16A and 16B which extend generally parallel to the longitudinal axis L and may be straight or curved. The size and absorbent capacity of the absorbent core 15 may also be varied to accommodate a variety of wearers. However, the total absorbent capacity of the absorbent core 15 should be compatible with the design loading and the intended use of the disposable absorbent article.

The absorbent core can contain conventional absorbent materials. In addition to conventional absorbent materials such as creped cellulose wadding, fluffed cellulose fibers, Rayon fibers, wood pulp fibers also known as airfelt or pulp fibers, and textile fibers, the core often includes superabsorbent material that imbibes fluids and form hydrogels. Such materials are also known as absorbent gelling materials (AGM) and may be included in particle form. AGM is typically capable of absorbing large quantities of body fluids and retaining them under moderate pressures. Synthetic fibers including cellulose acetate, polyvinyl fluoride, polyvinylidene chloride, acrylics (such as ORLON), polyvinyl acetate, non-soluble polyvinyl alcohol, polyethylene, polypropylene, polyamides (such as nylon), polyesters, bicomponent fibers, tricomponent fibers, mixtures thereof and the like can also be used in the secondary storage layer. The core can also include filler materials, such as PERLITE, diatomaceous earth, VERMICULITE, or other suitable materials, that lower rewet problems.

In certain embodiments, the absorbent core is an airlaid absorbent core comprising pulp fibers, absorbent gelling material, and bicomponent fibers. The absorbent core may comprise a basis weight of at least about 100 gsm, or at least about 140 gsm, or at least about 144 gsm, or at least about 150 gsm, or at least about 160 gsm, or at least about 165 gsm, or at least about 170 gsm, or from about 140 gsm to about 185 gsm, reciting for said range every 5 gsm increment therein.

The absorbent core may have AGM in a uniform distribution or may have AGM in a non-uniform distribution. The AGM may be in the in the form of channels, pockets, stripes, criss-cross patterns, swirls, dots, or any other pattern, either two or three dimensional, that can be imagined by man. The AGM may be sandwiched between a pair of fibrous cover layers. Or AGM may be encapsulated, at least in part, by a single fibrous cover layer.

Portions of the absorbent core can be formed only of superabsorbent material or can be formed of superabsorbent materials dispersed in a suitable carrier such as cellulose fibers in the form of fluff or stiffened fibers. One example of a non-limiting absorbent core is a first layer formed only of superabsorbent material that is disposed on a second layer that is formed from a dispersion of superabsorbent material within cellulose fibers.

Detailed examples of absorbent cores formed of layers of superabsorbent material and/or layers of superabsorbent material dispersed within cellulose fibers that may be utilized in the absorbent articles (e.g., sanitary napkins, incontinence products) detailed herein are disclosed in U.S. Patent Publication No. 2010/0228209 A1. Absorbent cores comprising relatively high amounts of SAP with various core designs are disclosed in U.S. Pat. No. 5,599,335 to Goldman et al., EP 1,447,066 to Busam et al., WO 95/11652 to Tanzer et al., U.S. Pat. Publ. No. 2008/0312622A1 to Hundorf et al., WO 2012/052172 to Van Malderen, U.S. Pat. No. 8,466,336 to Carlucci, and U.S. Pat. No. 9,693,910 to Carlucci.

The absorbent core 15 of the present disclosure may comprise any suitable shape including but not limited to an oval, a discorectangle, a rectangle, an asymmetric shape, and an hourglass. For example, in some forms of the present invention, the absorbent core 205 may comprise a contoured shape, e.g. narrower in the intermediate region than in the end regions. As yet another example, the absorbent core may comprise a tapered shape having a wider portion in one end region of the pad which tapers to a narrower end region in the other end region of the pad. The absorbent core 15 may comprise varying stiffness in the MD and CD.

Backsheet

The backsheet 14 may be positioned adjacent a garment-facing surface of the absorbent core 15. The backsheet 14 may be at least peripherally joined to the topsheet and/or to the core, and may be joined thereto by attachment methods such as those well known in the art. For example, the backsheet 14 may be secured to the absorbent core 15 by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of these attachment methods as are known in the art.

The backsheet 14 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 207 may prevent, or at least inhibit, the exudates absorbed and contained in the absorbent core 205 from wetting articles of clothing which contact the incontinence pad 10 such as undergarments. However, the backsheet 14 may permit vapors to escape from the absorbent core 15 (i.e., is breathable) while in some cases the backsheet 14 may not permit vapors to escape (i.e., non-breathable). Thus, the backsheet 14 may comprise a polymeric film such as thermoplastic films of polyethylene or polypropylene. A suitable material for the backsheet 14 is a thermoplastic film having a thickness of from about 0.012 mm (0.5 mil) to about 0.051 mm (2.0 mils), for example. Any suitable backsheet known in the art may be utilized with the present invention.

The backsheet 14 acts as a barrier to any absorbed bodily fluids that may pass through the absorbent core 15 to the garment surface thereof with a resulting reduction in risk of staining undergarments or other clothing. A preferred material is a soft, smooth, compliant, liquid and vapor pervious material that provides for softness and conformability for comfort, and is low noise producing so that movement does not cause unwanted sound.

Exemplary backsheets are described in U.S. Pat. No. 5,885,265 (Osborn, III.) issued Mar. 23, 1999; U.S. Pat. No. 6,462,251 (Cimini) issued Oct. 8, 2002; U.S. Pat. No. 6,623,464 (Bewick-Sonntag) issued Sep. 23, 2003 or U.S. Pat. No. 6,664,439 (Arndt) issued Dec. 16, 2003. Suitable dual or multi-layer breathable backsheets for use herein include those exemplified in U.S. Pat. Nos. 3,881,489, 4,341,216, 4,713,068, 4,818,600, EP 203 821, EP 710 471, EP 710 472, and EP 793 952.

Suitable breathable backsheets for use herein include all breathable backsheets known in the art. In principle there are two types of breathable backsheets, single layer breathable backsheets which are breathable and impervious to liquids and backsheets having at least two layers, which in combination provide both breathability and liquid imperviousness. Suitable single layer breathable backsheets for use herein include those described for example in GB A 2184 389, GB A 2184 390, GB A 2184 391, U.S. Pat. Nos. 4,591,523, 3,989,867, 3,156,242 and WO 97/24097.

The backsheet may be a nonwoven web having a basis weight between about 20 gsm and about 50 gsm. In one embodiment, the backsheet is a relatively hydrophobic 23 gsm spunbonded nonwoven web of 4 denier polypropylene fibers available from Fiberweb Neuberger, under the designation F102301001. The backsheet may be coated with a non-soluble, liquid swellable material as described in U.S. Pat. No. 6,436,508 (Ciammaichella) issued Aug. 20, 2002.

The backsheet has a garment-facing side and an opposite body-facing side. The garment-facing side of the backsheet comprises a non-adhesive area and an adhesive area. The adhesive area may be provided by any conventional means. Pressure sensitive adhesives have been commonly found to work well for this purpose.

Combination of Layers

The topsheet and the backsheet may be joined together to form an outer periphery of the disposable absorbent article. A periphery of the absorbent core and/or the fluid management layer may be disposed inboard of the outer periphery. For example, the absorbent core may have end edges extending generally parallel to a transverse axis and side edges extending generally parallel to a longitudinal axis. Each of the end edges and side edges may be disposed inboard of the outer periphery. Similarly, the fluid management layer may comprise end edges which extend generally parallel to the transverse axis and side edges which extend generally parallel to the longitudinal axis. The end edges and side edges may be disposed inboard of the outer periphery. Or, the end edges may be coterminous with the outer periphery to the extent that the end edges intersect the outer periphery. In addition, or independently of the end edges of the fluid management layer, the side edges of the fluid management layer may be coterminous with the outer periphery of the absorbent article.

Additionally, the end edges and/or side edges of the absorbent core and/or fluid management layer may be curvilinear in nature. For example, the side edges of the absorbent core and/or the fluid management layer may curve inward from the ends toward the transverse axis. Such construction may help with conformity of the absorbent article. Similarly, the end edges in conjunction with or independently of the side edges of the absorbent core and/or fluid management layer may comprise a curvilinear path which is either generally concave or generally convex.

The layers may be joined by any suitable means, including for example adhesive bonding, mechanical bonding, ultrasonic bonding and combinations thereof. Bonding may be continuous or discontinuous.

The inventors have surprisingly found the combination of layers of the present invention, results in a soft and dry feeling article that retains its shape despite compression and friction during wear (i.e., the article is resilient). As mentioned above, the topsheet may comprise a plurality of macro deformations, which may be in the form of apertures and/or recessions, which may reduce contact area between the article and the wearer's skin and thereby reduce the likelihood of sticking, abrasion, or wet feel. Further, one or more features may provide porosity to the article, providing an airy and comfortable feeling to the wearer. Such features may include high basis weight nonwovens, air through bonded nonwovens, and/or macro deformations. In nonlimiting examples, the topsheet, fluid management layer and/or absorbent core may be void of film materials.

In certain embodiments, two or more layers may complement one another to provide appropriate stiffness to the final article. In typical liner articles, layers on the wearer facing side of the absorbent core essentially have no measurable stiffness according to the 3 Point Bend test method herein. In articles of the present invention, the fluid management layer may comprise more rigidity than known fluid management layers. In combination with a topsheet and absorbent core of the present invention, the article may be provided with better stiffness. In nonlimiting examples, the fluid management layer may comprise a MD stiffness of at least about 0.03 N (Peak Load), or at least at about 0.05 N (Peak Load), or from about 0.03 N (Peak Load) to about 0.07 N (Peak Load) according to the 3 Point Bend test method herein. The fluid management layer may comprise a CD stiffness of at least about 0.01 N(Peak Load), or from about 0.005 N (Peak Load) to about 0.05 N (Peak Load), or from about 0.01 N (Peak Load) to about 0.03 N (Peak Load), reciting for each range every 0.005 increment therein. Additionally, or alternatively, the absorbent core may comprise a MD stiffness of at least about 0.1 N (Peak Load), or at least about 0.15 N (Peak Load), or at least about 0.2 N (Peak Load), or from about 0.08 N (Peak Load) to about 2 N (Peak Load), reciting for said range every 0.05 increment therein, according to the 3 Point Bend test method herein. The absorbent core may comprise a CD stiffness of at least about 0.1 N (Peak Load), or at least about 0.13 N (Peak Load), or at least about 0.16 N (Peak Load), or from about 0.7 N (Peak Load) to about 0.18 N (Peak Load), or from about 0.9 N (Peak Load) to about 0.16 N (Peak Load) according to the 3 Point Bend test method herein.

Additionally, or alternatively, two or more layers may complement one another to provide a gradual change in porosity, such that collectively the article feels airy/breathable while maintaining structural integrity and trapping fluid below the surface to prevent rewet. In nonlimiting examples, the topsheet may comprise a porosity of about at least about 300 m$^3$/m$^2$/min, or from about 300 m$^3$/m$^2$/min to about 400 m$^3$/m$^2$/min, or from about 320 m$^3$/m$^2$/min to about 380 m$^3$/m$^2$/min, or from about 330 m$^3$/m$^2$/min to about 360 m$^3$/m$^2$/min, or about 340 m$^3$/m$^2$/min to about 350 m$^3$/m$^2$/min, reciting for each range every 1 m$^3$/m$^2$/min increment therein according to the Air Permeability test method herein. The topsheet may comprise a porosity that is greater than that of the fluid management layer. The fluid management layer may comprise a porosity of at least about 200 m$^3$/m$^2$/min, or from about 200 m$^3$/m$^2$/min to about 350 m$^3$/m$^2$/min, or from about 250 m$^3$/m$^2$/min to about 325 m$^3$/m$^2$/min, or from about 275 m$^3$/m$^2$/min to about 310 m$^3$/m$^2$/min, or about 290 m$^3$/m$^2$/min to about 300 m$^3$/m$^2$/min, reciting for each range every 1 m$^3$/m$^2$/min increment therein, according to the Air Permeability test method herein. In nonlimiting examples, the topsheet may be within about 20% or less, or about 15% or less, or within about 5% to about 20% of the porosity of the fluid management layer, as measured by taking the higher of the two permeability values subtracting the lesser of the two and dividing the difference by the higher of the two values. Additionally, or alternatively, the absorbent core may comprise a porosity of at least about 25 m$^3$/m$^2$/min, or at least about 30 m$^3$/m$^2$/min, or from about 25 m$^3$/m$^2$/min to about 60 m$^3$/m$^2$/min, or from about 30 m$^3$/m$^2$/min to about 50 m$^3$/m$^2$/min, or from 35 m$^3$/m$^2$/min to about 45 m$^3$/m$^2$/min, reciting for each range every 1 m$^3$/m$^2$/min increment therein, according to the Air Permeability test method herein. The fluid management layer may be within about 90% or less, or about 86% or less, or from about 25% to about 90%, or from about 45% to about 88%, or from about 60% to about 80% of the porosity of the absorbent core, reciting for each range every 2% increment therein, according to the Air Permeability test method herein.

In certain embodiments, the article comprises a gradient of increasing porosity at the transverse centerline in a first z-direction. By gradient it is meant that in the assembled article, porosity differs along the z-direction. The first z-direction extends from the backsheet towards the topsheet. The gradient may be present in areas outside of the barrier strips 18.

As mentioned, articles of the present invention retain their shape after wear, which is particularly useful where articles are liners which are worn for long periods of time. Indeed, many individuals wear a liner for 8 hours or more. As such, liner wearers desire an article that will not stick to the skin, deform and/or fold over even after extended periods of wear. Moreover, wearers having a high body mass index (i.e., a BMI of at least 30) desire products that can maintain their shape and withstand high compression, regardless of the duration of wear. Articles of the present invention may address these needs.

Further to the above, an article of the present invention provides sufficient integrity to prevent bunching, i.e., rolling or folding in the x-y direction due to compression of the legs during wear. The article may exhibit a Wet CD Bunch Compression of at least about 310 gf, or at least about 325 gf, or at least about 350 gf, or at least about 400 gf, or from about 310 gf to about 550 gf, or from about 325 gf to about 500 gf, or from about 400 gf to about 475 gf, reciting for each range every 10 gf increment therein. Additionally, or alternatively, the article may exhibit a Wet CD Bunch Compression Recovery of about 40% or greater, or about 42% or greater, or from about 40% to about 50%, or from about 42% to about 45%, reciting for each range every 1% increment therein. The article may exhibit a Dry CD Bunch Compression of at least about 400 gf, or at least about 450 gf, or at least about 475 gf, or at least about 500 gf, or from about 400 gf to about 625 gf, or from about 450 gf to about 520 gf, reciting for each range every 10 gf increment therein. Additionally, or alternatively, the article may exhibit a Dry CD Bunch Compression Recovery of about 40% or greater, or about 48% or greater, or about 50% or greater, or about 52% or greater, or from about 40% to about 60%, or from about 50% to about 55%, reciting for each range every 1% increment therein. CD Bunch Compression and Bunch Compression Recovery values are obtained via the Bunch Compression test method.

In some embodiments, the article may a CD 3 Point Bend Stiffness of at least about 0.25 N, or at least about 0.3 N, or at least 0.35 N, or at least about 0.4, or from about 0.25 N to about 0.6 N, or from about 0.3 to about 0.5 N, reciting for each range every 0.1 N increment therein, according to the 3 Point Bend test method.

Notably, the above noted stiffness, recovery and/or bunch compression values may be achieved while maintaining suitable fluid management properties. Indeed, articles of the present invention exhibit high resiliency in z-direction, indicating reduced risk of fluid resurfacing after z-direction pressure, and desirable fluid acquisition properties.

In certain embodiments, an article of the present invention may exhibit a Z Compression Percent Recovery of at least about 70%, or at least about 74%, from about 70% to about 85%, or from about 74% to about 80%, reciting for each range every 1% increment therein according to the Z Compression test method herein.

Additionally, or alternatively, the article may exhibit an Energy to Compress of at least about 1.5 N*mm, or at least about 1.75 N*mm, or at least about 2 N*mm, or at least about 2.2 N*mm, or from about 2 N*mm to about 2.5 N*mm, reciting for said range every 0.1 N*mm increment therein, according to the Z Compression test method.

In certain embodiments, the article may exhibit an acquisition speed of less than about 10 seconds, less than about 5 seconds, less than about 3 seconds, or less than about 2.5 seconds, or from about 1 second to about 2.5 seconds, or from about 1.5 seconds to about 2.2 seconds when measured in accordance with the Liquid Acquisition Time test method described herein.

Additionally, or alternatively, the article may exhibit Urine Standard Rewet of about 10 mg or less, or about 5 mg or less, or about 2 mg or less, or about 1 mg or less, or undetectable, according to the Standard Rewet test method. The article may exhibit a Urine Instant Rewet of about 65 mg or less, or about 50 mg or less, about 25 mg or less, or about 5 mg or less, or about 4 mg or less, or undetectable, according to the Instant Rewet test method.

Disposable absorbent articles according to the present invention were constructed and tested. Additionally, comparative example disposable absorbent articles were constructed and tested.

Comparative Example 1 includes a two barrier stripes each comprising a 18 gsm spunbond nonwovens; a topsheet comprising a 14 gsm bicomponent fiber, spunbond nonwoven and a 22 gsm formed, apertured film and; and a fluid management layer/secondary topsheet comprising a 14 gsm bicomponent fiber, spunbond nonwoven, such that the 14 gsm nonwovens sandwich the apertured formed film. The article further includes a 170 gsm airlaid absorbent core comprising pulp fiber, absorbent gelling materials and bicomponent fibers. The article's backsheet comprises a 14.2 gsm polyethylene film. A pressure sensitive adhesive is slot coated on the backsheet at 12 gsm. The layers are bonded by adhesive. The product is available in Germany under the name ALWAYS DAILIES® Large EXTRA PROTECT®.

Comparative Example 2 includes a topsheet comprising a carded nonwoven having a basis weight of about 16 gsm and a formed apertured film layer having a basis weight of about 14 gsm. The article also includes a fluid management layer/secondary topsheet comprising an air through bonded nonwoven having a basis weight of about 36 gsm. The article further includes an airlaid absorbent core comprising pulp fiber and absorbent gelling materials, the absorbent core having a basis weight of about 178 gsm. The backsheet is a polymeric film having a basis weight of about 18.5 gsm. The product is available in Germany under the name CAREFREE® PLUS LARGE®.

Inventive Example 1 includes a topsheet having a basis weight of 24 gsm and being an air-through bonded, nonwoven with macro deformations (both apertures and recessions) formed thereon. The air-through bonded nonwoven comprises bicomponent fibers, where polyethylene terephthalate and polyethylene are in a core-sheath configuration with polyethylene is the sheath. The fibers comprise a 2.2 dtex. The topsheet comprises 60% hydrophilic fibers and 40% hydrophobic fibers by weight of the fibers. The fluid management layer is a 55 gsm integrated nonwoven having 20 percent by weight viscose cellulose fibers having a 1.7 dtex; 30 percent by weight hollow spiral polyethylene terephthalate fibers having a 10 dtex; and 50 percent by weight bi-component fibers having polyethylene terephthalate and polyethylene in a core-sheath configuration where the polyethylene is the sheath. The absorbent is a 170 gsm airlaid absorbent core having the same construction as the absorbent core in Comparative Example 1. The barrier strips, backsheet and pressure sensitive adhesive are the same as those of Comparative Example 1.

Inventive Example 2 includes a topsheet having a basis weight of 24 gsm and being an air-through bonded, nonwoven with macro deformations (both apertures and recessions) formed thereon. The air-through bonded nonwoven comprises bicomponent fibers, where polyethylene terephthalate and polyethylene are in a core-sheath configuration with polyethylene is the sheath. The fibers comprise a 2.2 dtex. The topsheet comprises 60% hydrophilic fibers and 40% hydrophobic fibers by weight of the fibers. The fluid management layer is a 45 gsm integrated nonwoven having 20 percent by weight viscose cellulose fibers having a 1.7 dtex; 30 percent by weight hollow spiral polyethylene terephthalate fibers having a 10 dtex; and 50 percent by weight bi-component fibers having polyethylene terephthalate and polyethylene in a core-sheath configuration where the polyethylene is the sheath. The absorbent is a 170 gsm airlaid absorbent core having the same construction as the absorbent core in Comparative Example 1. The barrier strips, backsheet and pressure sensitive adhesive are the same as those of Comparative Example 1.

Inventive Example 3 includes a topsheet having a basis weight of 24 gsm and being an air-through bonded, nonwoven with macro deformations (both apertures and recessions) formed thereon. The air-through bonded nonwoven comprises bicomponent fibers, where polyethylene terephthalate and polyethylene are in a core-sheath configuration with polyethylene is the sheath. The fibers comprise a 2.2 dtex. The topsheet comprises 60% hydrophilic fibers and 40% hydrophobic fibers by weight of the fibers. The fluid management layer is a 45 gsm integrated nonwoven having 20 percent by weight viscose cellulose fibers having a 1.7 dtex; 30 percent by weight hollow spiral polyethylene terephthalate fibers having a 10 dtex; and 50 percent by weight bi-component fibers having a first component polyethylene terephthalate and polyethylene in a core-sheath configuration where the polyethylene is the sheath. The absorbent is a 144 gsm airlaid absorbent core comprising pulp fiber, absorbent gelling materials and bicomponent fibers. The barrier strips, backsheet and pressure sensitive adhesive are the same as those of Comparative Example 1.

Inventive Example 4 includes a topsheet having a basis weight of 24 gsm and being an air-through bonded, nonwoven with macro deformations (both apertures and recessions) formed thereon. The air-through bonded nonwoven comprises bicomponent fibers, where polyethylene terephthalate and polyethylene are in a core-sheath configuration with polyethylene is the sheath. The fibers comprise a 2.2 dtex. The topsheet comprises 60% hydrophilic fibers and 40% hydrophobic fibers by weight of the fibers. The fluid management layer is a 55 gsm integrated nonwoven having 20 percent by weight viscose cellulose fibers having a 1.7 dtex; 30 percent by weight hollow spiral polyethylene terephthalate fibers having a 10 dtex; and 50 percent by weight bi-component fibers having a first component polyethylene terephthalate and polyethylene in a core-sheath configuration where the polyethylene is the sheath. The absorbent core is a 144 gsm airlaid absorbent core comprising pulp fiber, absorbent gelling materials and bicomponent fibers. The barrier strips, backsheet and pressure sensitive adhesive are the same as those of Comparative Example 1.

TABLE 1

|  | Comparative Example 1 | Comparative Example 2 | Inventive Example 1 | Inventive Example 2 | Inventive Example 3 | Inventive Example 4 |
| --- | --- | --- | --- | --- | --- | --- |
| CD Bunch Compression 1st cycle peak load (gf) Wet | 308 | 282 | 460 | 430 | 254 | 308 |
| CD Bunch Compression Recovery %-wet | 40 | 55 | 43 | 42 | 40 | 41 |
| CD Bunch Compression 1st cycle peak load (gf) Dry | 428 | 522 | 515 | 515 | 283 | 617 |
| CD Bunch Compression Recovery %-Dry | 47 | 50 | 54 | 50 | 43 | 47 |
| 3 point CD Bend Stiffness (Peak Load N) | 0.24 | 0.53 | 0.42 | 0.42 | 0.34 | 0.37 |
| Energy to Compress Z compression (N · mm) | 1.64 | 2.92 | 2.35 | 2.02 | 2.02 | 2.05 |
| % Recovery Z compression test | 72 | 73 | 74 | 74 | 74 | 74 |
| 3 ml load Liner Standard Re-wet Test Synthetic Urine Fluid (g) | 0.002 | 0 | 0 | 0 | 0 | 0 |
| 3 ml load instant Re-wet Test Synthetic Urine Fluid (g) | 0.025 | 0.005 | 0 | 0.004 | 0.047 | 0.065 |
| 3 ml Urine Acquisition Speed (Sec) | 2.54 | n/a | 2.01 | 1.65 | 2.19 | 1.72 |

As can be seen in Table 1, the inventive examples provide higher Percent Recovery Z Compression than known articles. In addition, two of the inventive examples provide higher Wet CD Bunch Compression than known articles, signifying the retention of article shape and placement during wear. Further still, when viewing the combination of results above, the inventive examples are able to achieve parity or better performance in acquisition and rewet but without a film layer.

Release Paper

The adhesive coated on the backsheet surface are typically provided with a protective cover, which is removed prior to use. The protective cover may be a silicone coated release paper, a plastic film or any other easily removable cover. The protective cover may be in a single piece or in a multitude of pieces, e.g. to cover the individual adhesive areas. It also can perform other functions such as providing individualized packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

Test Methods

Bunch Compression Test

Bunched Compression of a sample is measured on a constant rate of extension tensile tester (a suitable instrument is the MTS Alliance using Testworks 4.0 software or TestSuite software, as available from MTS Systems Corp., Eden Prairie, MN, or equivalent) using a load cell for which the forces measured are within 1% to 99% of the limit of the cell. All testing is performed in a room controlled at 23° C.±3 C° and 50%±2% relative humidity. The test can be performed wet or dry.

Figure 6:
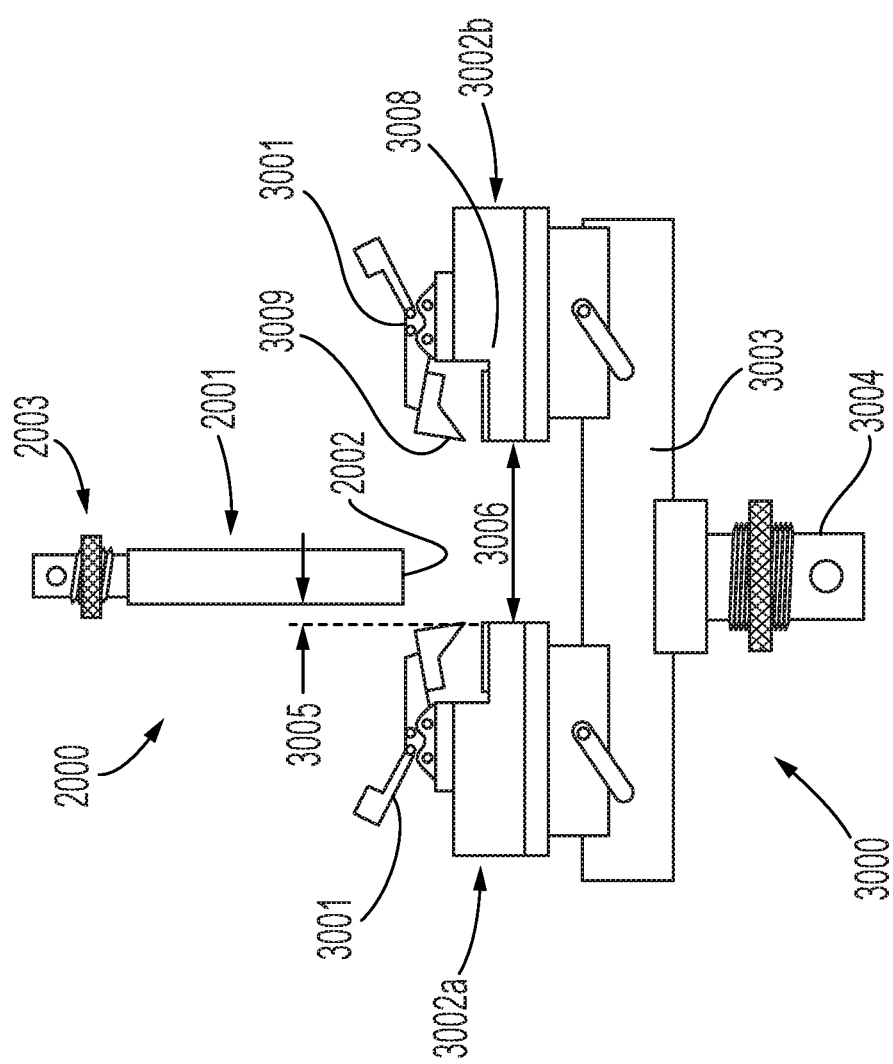
FIGS. 6-7B is a schematic representation of test apparatus for the Bunch Compression method disclosed herein.

As shown in FIG. 6, the bottom stationary fixture 3000 consists of two matching sample clamps 3001 each 100 mm wide each mounted on its own movable platform 3002a, 3002b. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Samples are conditioned at 23° C.±3 C° and 50%±2% relative humidity for at least 2 hours before testing. When testing a whole article, remove the release paper from any panty fastening adhesive on the garment facing side of the article. Lightly apply talc powder to the adhesive to mitigate any tackiness. If there are cuffs, excise them with scissors, taking care not to disturb the top sheet of the product. Place the article, body facing surface up, on a bench. On the article identify the intersection of the longitudinal midline and the lateral midline. Using a rectangular cutting die, cut a specimen 100 mm in the longitudinal direction by 80 mm in the lateral direction, centered at the intersection of the midlines. When testing just the absorbent body of an article, place the absorbent body on a bench and orient as it will be integrated into an article, i.e., identify the body facing surface and the lateral and longitudinal axis. Using a rectangular cutting die, cut a specimen 100 mm in the longitudinal direction by 80 mm in the lateral direction, centered at the intersection of the midlines.

The specimen can be analyzed both wet and dry. The dry specimen requires no further preparation. The wet specimens are dosed with 0.9% w/v saline solution (i.e., 9.0 g of NaCl diluted to 1 L deionized water). A 7 mL dose of the 0.9% w/v saline solution is applied to the test sample using a calibrated Eppendorf-type pipettor, spreading the fluid over the complete body facing surface of the specimen within a period of approximately 3 sec. The wet specimen is tested 10.0 min±0.1 min after the dose is applied.

Program the tensile tester to zero the load cell, then lower the upper fixture at 2.00 mm/sec until the contact surface of the plunger touches the specimen and 2 gf is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 100 Hz during all compression/decompression cycles.

Figure 7A:
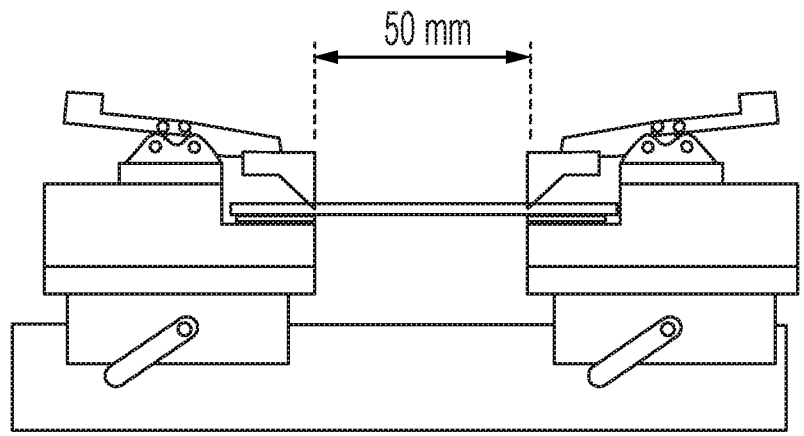
Figure 7B:
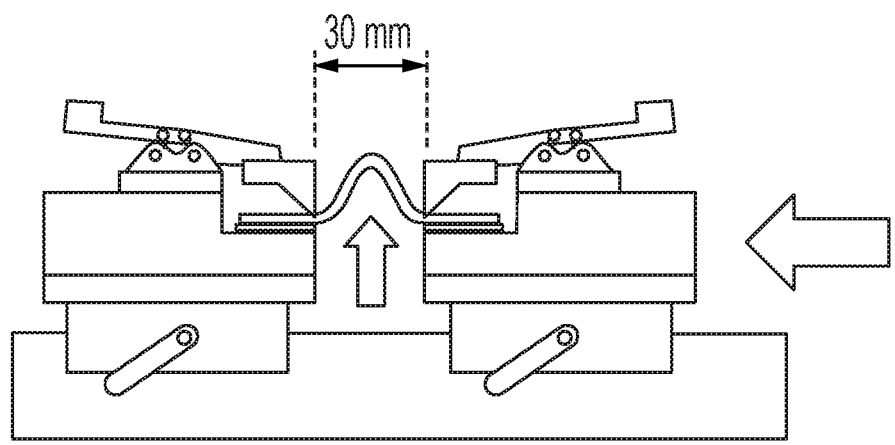

Position the left platform 3002a 2.5 mm from the side of the upper plunger (distance 3005). Lock the left platform into place. This platform 3002a will remain stationary throughout the experiment. Align the right platform 3002b 50.0 mm from the stationary clamp (distance 3006). Raise the upper probe 2001 such that it will not interfere with loading the specimen. Open both clamps. Referring to FIG. 7A, place the specimen with its longitudinal edges (i.e., the 100 mm long edges) within the clamps. With the specimen laterally centered, securely fasten both edges. Referring to FIG. 7B, move the right platform 3002b toward the stationary platform 3002a a distance 30.0 mm. Allow the specimen to bow upward as the movable platform is positioned. Manually lower the probe 2001 until the bottom surface is approximately 1 cm above the top of the bowed specimen.

Figure 8A:
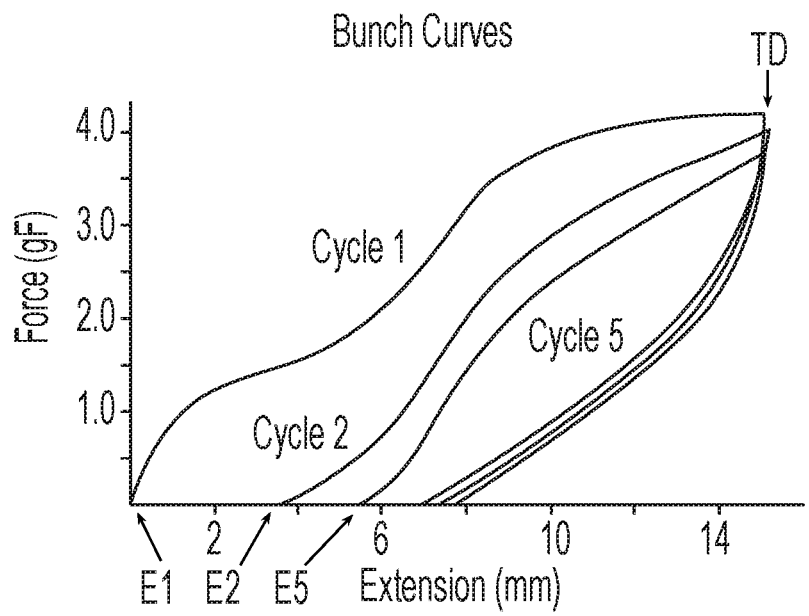
FIGS. 8A-8B are charts exhibiting representative Force/Extension Curves for the Bunch Compression method disclosed herein.
Figure 8B:
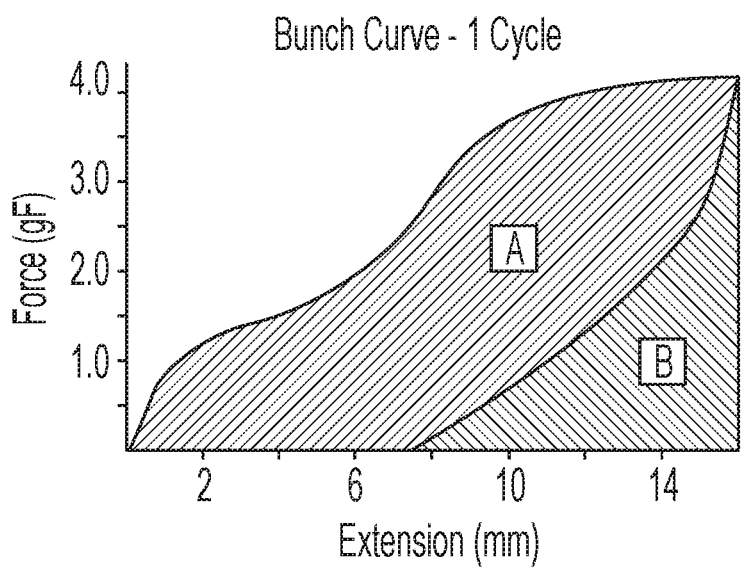

Start the test and collect displacement (mm) verses force (gf) data for all five cycles. Construct a graph of Force (gf) versus displacement (mm) separately for all cycles. A representative curve is shown in FIG. 8A. From the curve record the Maximum Compression Force for each Cycle and report to the nearest 1 gf as the CD Bunch Compression for the Cycle. Calculate the % Recovery between the First and Second cycle as (TD-E2)/(TD-E1)*100 where TD is the total displacement and E2 is the extension on the second compression curve that exceeds 2.0 gf. Record to the nearest 0.01%. In like fashion calculate the % Recovery between the First Cycle and other cycles as (TD-Ei)/(TD-E1)*100 and report to the nearest 0.01%. Referring to FIG. 8B, calculate the Energy of Compression for Cycle 1 as the area under the compression curve (i.e., area A+B) and record to the nearest 0.1 gf*mm. Calculate the Energy Loss from Cycle 1 as the area between the compression and decompression curves (i.e., Area A) and report to the nearest 0.1 gf*mm. Calculate the Energy of Recovery for Cycle 1 as the area under the decompression curve (i.e. Area B) and report to the nearest 0.1 gf*mm. In like fashion calculate the Energy of Compression (gf*mm), Energy Loss (gf*mm) and Energy of Recovery (gf*mm) for each of the other cycles and record to the nearest 0.1 gf*mm. For each sample, analyze a total of five (5) replicates and report the arithmetic mean for each parameter. All results are reported specifically as Dry or Wet.

3 Point Bend Test

The bending properties of a sample are measured on a constant rate of extension tensile tester (a suitable instrument is the MTS Alliance using Testworks 4.0 Software or TestSuite Software, as available from MTS Systems Corp., Eden Prairie, MN) using a load cell for which the forces measured are within 1% to 99% of the limit of the cell. All testing is performed in a room controlled at 23° C.±3 C and 50%±2% relative humidity.

The bottom stationary fixture consists of two bars 3.175 mm in diameter by 60 mm in length, made of polished stainless steel each mounted on its own fork. These 2 bars are mounted horizontally, aligned front to back and parallel to each other, with top radii of the bars vertically aligned. Furthermore, the fixture allows for the two bars to be move horizontally away from each other on a track so that a gap can be set between them while maintaining their orientation. The top fixture consists of a third bar also 3.175 mm in diameter by 60 mm in length, made of polished stainless steel mounted on a fork. When in place the bar of the top fixture is parallel to and aligned front to back with the bars of the bottom fixture. Both fixtures include an integral adapter appropriate to fit the respective position on the tensile tester frame and lock into position such that the bars are orthogonal to the motion of the crossbeam of the tensile tester.

Set the gap between the bars of the lower fixture to 25 mm±0.5 mm (center of bar to center of bar) with the upper bar centered at the midpoint between the lower bars. Set the gage (bottom of top bar to top of lower bars) to 1.0 cm.

Samples are conditioned at 23° C.±3° C. and 50%±2% relative humidity two hours prior to testing. Cut a specimen 50.8 mm in the longitudinal direction of the article (MD) and 50.8 mm in the lateral direction (CD) of the article from the center of the article maintaining their orientation after they are cut. Specimens are taken from an area that is free of folds. Measure the caliper of each specimen, using a digital caliper (e.g. Ono Sokki GS-503 or equivalent) fitted with a 25 mm diameter foot that applies a confining pressure of 0.1 psi. Read the caliper (mm) 5 sec after resting the foot on the sample and record to the nearest 0.01 mm.

Program the tensile tester for a flexural bend test, to move the crosshead such that the top fixture moves down with respect to the lower fixture at a rate of 1.0 mm/sec until the upper bar touches the top surface of the specimen, then continue for an additional 12 mm collecting force (N) and displacement (mm) data at 100 Hz, and return the crosshead to its original gage.

Load a specimen such that it spans the two lower bars centered under the upper bar with its sides parallel to the bars. For the MD orientation, the MD direction is perpendicular to the length of the 3 bars. For the CD orientation, the CD direction is perpendicular to the length of the bars. Zero the crosshead and load cell. Start the run and collect data.

Construct a graph of force (N) verses displacement (mm). From the graph, record the maximum peak force to the nearest 0.01 N. In like fashion, repeat the entire test sequence for 3 MD and 3 CD test specimens. Calculate the arithmetic mean of the maximum peak force for the replicates at each orientation (MD and CD) and report as 3 Point Bend Stiffness to the nearest 0.01 N, noting the orientation with the reported value.

Liquid Acquisition Time

Liquid Acquisition Time is measured for a test sample insulted with a known volume of test liquid, using a strikethrough plate and an electronic circuit interval timer described in compendial method WSP 70.3. The time required for the test liquid to pass into the test sample is recorded. Subsequent to the liquid acquisition test, a rewet test is performed on the test sample (described separately, herein). All measurements are performed in a laboratory maintained at 23° C.±2 C° and 50%±2% relative humidity and test samples are conditioned in this environment for at least 2 hours prior to testing.

The test liquid used for this liquid acquisition test includes the following reagent grade components available from VWR International (or an equivalent source): Urea ($NH_2CONH_2$, CAS No 57-13-6), Sodium Chloride (NaCl, CAS No 7647-14-5), Magnesium Sulfate Heptahydrate ($MgSO_4$ $7H_2O$, CAS No 10034-99-8), Calcium Chloride anhydrous ($CaCl_2$), CAS No 10043-52-4) and deionized water. To prepare the test liquid, add 2.0% w/v Urea, 0.90% w/v Sodium Chloride, 0.11% w/v Magnesium Sulfate Heptahydrate, 0.06% w/v Calcium Chloride anhydrous to a sufficiently sized volumetric flask. Then fill with deionized water (quantity sufficient) and mix thoroughly. The test liquid is used at room temperature.

The test apparatus includes a strikethrough plate, a baseplate, an electronic timer, a funnel with a magnetic valve to discharge the dose of test liquid and a ring stand to hold the funnel, in accordance with the apparatus descriptions described in compendial method WSP 70.3. A suitable apparatus is the Lister AC available from Lenzing Instruments GmbH & Co (Gampern, Austria). In addition, a micro pipette capable of delivering a 3.0 mL dose of test liquid is used.

Test samples are prepared by removing the absorbent article from any outer packaging, and if the article is folded, unfold it and extend the wings if present. The protective layer covering the panty fastening adhesive can be left in place. The test location is the intersection of the longitudinal and lateral midpoints of the absorbent article. Condition the test samples as previously described prior to testing.

Measure the liquid acquisition time as follows. The test sample is placed onto the baseplate, centering the test location over the plate. Place the strikethrough plate on top of the test sample with the test location centered under the center of the plate's orifice. Now place the entire stack of baseplate, test sample and strikethrough plate under the funnel, ensuring the test location is centered under the funnel. Adjust the height of the funnel so that it is 5±1 mm above the top surface of the strikethrough plate (i.e. 30 mm above the top surface of the test sample). Connect the electrodes of the strikethrough plate to the electronic timer and ensure the timer is set to zero. With the discharge valve of the funnel closed, use a micro pipette to dispense 3.0 mL of the test liquid into the funnel. Open the magnetic discharge valve of the funnel to discharge the 3.0 mL of test liquid into the reservoir of the strikethrough plate. The electronic timer will start as soon as the test liquid makes contact with the electrodes and will stop once the test liquid falls below the level of the electrodes (i.e. the entire liquid dose has penetrated into the test sample). Record the time indicated on the electronic timer to the nearest 0.01 seconds. The test sample is then immediately evaluated by one of the rewet tests described separately, herein (Standard Rewet or Instant Rewet). Prior to testing the next sample, the electrodes and strikethrough plate are cleaned with deionized water and dried completely.

In like fashion, the test sequence is repeated for five replicate test samples. Calculate and report Liquid Acquisition Time as the arithmetic mean of the replicates to the nearest 0.01 seconds.

Standard Rewet

Standard Rewet is measured on a test sample 20 minutes after the Liquid Acquisition test (described separately, herein). Rewet is the amount of liquid that emerges from a previously wetted test sample when a weight is applied. All measurements are performed in a laboratory maintained at 23° C.±2 C° and 50%±2% relative humidity.

The rewet weight is constructed of stainless steel, or equivalent, such that the dimensions of the bottom face of the weight are 4.5 cm by 10 cm and the total mass of the weight is 3150 g, including any handle that might be attached. A mechanical device can be constructed, if needed, to aid in the lowering and raising of the rewet weight.

For each test sample, two plies of filter paper cut to 150 mm diameter are used as the rewet substrate. The filter paper is conditioned at 23° C.±2 C° and 50%±2% relative humidity for at least 2 hours prior to testing. A suitable filter paper has a basis weight of about 85 gsm, a thickness of about 180 microns with medium porosity, and is available from VWR International as Whatman grade 597.

Obtain the mass of 2 plies of the filter paper and record as Dry Mass$_{fp}$ to the nearest 0.001 grams. When 20 minutes have elapsed after the Liquid Acquisition test, gently remove the strikethrough plate from the test sample and set aside. Place the 2 plies of pre-weighed filter paper onto the test sample, centering the stack over the dosing location. Now place the rewet weight centered over the top of the filter papers and start a 15 second timer. As soon as 15 seconds have elapsed, gently remove the rewet weight and set aside. Obtain the mass of the 2 plies of filter paper and record as Wet Mass$_{fp}$ to the nearest 0.001 grams. Subtract the Dry Mass$_{fp}$ from the Wet Mass$_{fp}$ and report as Standard Rewet to the nearest 0.001 grams. Wipe off any residual test liquid from the bottom face of the rewet weight prior to testing the next sample.

In like fashion, repeat the entire procedure for five replicate samples. Calculate and report Standard Rewet as the arithmetic mean of the replicates to the nearest 0.001 grams.

Instant Rewet

Instant Rewet is measured on a test sample 1 minute after the Liquid Acquisition test (described separately, herein). Rewet is the amount of liquid that emerges from a previously wetted test sample when a weight is applied. All measurements are performed in a laboratory maintained at 23° C.±2 C° and 50%±2% relative humidity.

The rewet weight is constructed of stainless steel, or equivalent, such that the dimensions of the bottom face of the weight are 4.5 cm by 10 cm and the total mass of the weight is 3150 g, including any handle that might be attached. A mechanical device can be constructed, if needed, to aid in the lowering and raising of the rewet weight.

For each test sample, two plies of filter paper cut to 150 mm diameter are used as the rewet substrate. The filter paper is conditioned at 23° C.±2 C° and 50%±2% relative humidity for at least 2 hours prior to testing. A suitable filter paper has a basis weight of about 85 gsm, a thickness of about 180 microns with medium porosity, and is available from VWR International as Whatman grade 597.

Obtain the mass of 2 plies of the filter paper and record as Dry Mass$_{fp}$ to the nearest 0.001 grams. When 1 minute has elapsed after the Liquid Acquisition test, gently remove the strikethrough plate from the test sample and set aside. Place the 2 plies of pre-weighed filter paper onto the test sample, centering the stack over the dosing location. Now place the rewet weight centered over the top of the filter papers and start a 15 second timer. As soon as 15 seconds have elapsed, gently remove the rewet weight and set aside. Obtain the mass of the 2 plies of filter paper and record as Wet Mass$_{fp}$ to the nearest 0.001 grams. Subtract the Dry Mass$_{fp}$ from the Wet Mass$_{fp}$ and report as Instant Rewet to the nearest 0.001 grams. Wipe off any residual test liquid from the bottom face of the rewet weight prior to testing the next sample.

In like fashion, repeat the entire procedure for five replicate samples. Calculate and report Instant Rewet as the arithmetic mean of the replicates to the nearest 0.001 grams.

Air Permeability

Air permeability is the velocity of air flow passing perpendicularly through a test specimen under specified conditions of test area and pressure drop. Air permeability is measured in accordance with compendial method WSP 70.1 for a test area of 20 cm$^2$ and a pressure drop of 125 Pa using a test apparatus as described within the method. A suitable instrument is the FX3300 Air Permeability Tester available from Textest AG (Schwerzenbach, Switzerland), or equivalent. All measurements are performed in a laboratory maintained at 23° C.±2 C° and 50%±2% relative humidity and test samples are conditioned in this environment for at least 2 hours prior to testing.

Measurements are made on test specimens taken from rolls or sheets of the raw material, or test specimens obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained. The test specimen must be as large as possible so that any inherent material variability is accounted for, and it must be larger than the 20 cm$^2$ test orifice.

Measure the air permeability of the test specimen with a 20 cm$^2$ orifice at a pressure drop of 125 Pa and record to the nearest 0.1 m$^3$/m$^2$/min. In like fashion, repeat for a total of ten replicate test specimens. Calculate the arithmetic mean for Air Permeability and report to the nearest 0.1 m$^3$/m$^2$/min for each specific material layer being evaluated.

Caliper

The caliper, or thickness, of a test specimen is measured as the distance between a reference platform on which the specimen rests and a pressure foot that exerts a specified amount of pressure onto the specimen over a specified amount of time. All measurements are performed in a laboratory maintained at 23° C.±2 C° and 50%±2% relative humidity and test specimens are conditioned in this environment for at least 2 hours prior to testing.

Caliper is measured with a manually-operated micrometer equipped with a pressure foot capable of exerting a steady pressure of 0.50 kPa±0.01 kPa onto the test specimen. The manually-operated micrometer is a dead-weight type instrument with readings accurate to 0.01 mm. A suitable instrument is Mitutoyo Series 543 ID-C Digimatic, available from VWR International, or equivalent. The pressure foot is a flat ground circular movable face with a diameter that is smaller than the test specimen and capable of exerting the required pressure. A suitable pressure foot has a diameter of 25.4 mm, however a smaller or larger foot can be used depending on the size of the specimen being measured. The test specimen is supported by a horizontal flat reference platform that is larger than and parallel to the surface of the pressure foot. The system is calibrated and operated per the manufacturer's instructions.

Obtain a test specimen by removing it from an absorbent article, if necessary. When excising the test specimen from an absorbent article, use care to not impart any contamination or distortion to the test specimen layer during the process. The test specimen is obtained from an area free of folds or wrinkles, and it must be larger than the pressure foot.

To measure caliper, first zero the micrometer against the horizontal flat reference platform. Place the test specimen on the platform with the test location centered below the pressure foot. Gently lower the pressure foot with a descent rate of 3.0 mm±1.0 mm per second until the full pressure is exerted onto the test specimen. Wait 5 seconds and then record the caliper of the test specimen to the nearest 0.001 mm. In like fashion, repeat for a total of ten replicate test specimens. Calculate the arithmetic mean for all caliper measurements and report as Caliper to the nearest 0.001 mm.

Caliper Factor

The caliper factor, as mentioned previously is the caliper per 10 gsm of basis weight of the sample. So, the equation is caliper/(basis weight/10).

Basis Weight

The basis weight of a test sample is the mass (in grams) per unit area (in square meters) of a single layer of material and is measured in accordance with compendial method WSP 130.1. The mass of the test sample is cut to a known area, and the mass of the sample is determined using an analytical balance accurate to 0.0001 grams. All measurements are performed in a laboratory maintained at 23° C.±2 C° and 50%±2% relative humidity and test samples are conditioned in this environment for at least 2 hours prior to testing.

Measurements are made on test samples taken from rolls or sheets of the raw material, or test samples obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained. The test specimen must be as large as possible so that any inherent material variability is accounted for.

Measure the dimensions of the single layer test specimen using a calibrated steel metal ruler traceable to NIST, or equivalent. Calculate the Area of the test specimen and record to the nearest 0.0001 square meter. Use an analytical balance to obtain the Mass of the test specimen and record to the nearest 0.0001 gram. Calculate Basis Weight by dividing Mass (in grams) by Area (in square meters) and record to the nearest 0.01 grams per square meter (gsm). In like fashion, repeat for a total of ten replicate test specimens. Calculate the arithmetic mean for Basis Weight and report to the nearest 0.01 grams/square meter.

Material Compositional Analysis

The quantitative chemical composition of a test specimen comprising a mixture of fiber types is determined using ISO 1833-1. All measurements are performed in a laboratory maintained at 23° C.±2 C° and 50%±2% relative humidity.

Analysis is performed on test samples taken from rolls or sheets of the raw material, or test samples obtained from a material layer removed from an absorbent article. When excising the material layer from an absorbent article, use care to not impart any contamination or distortion to the layer during the process. The excised layer should be free from residual adhesive. To ensure that all adhesive is removed, soak the layer in a suitable solvent that will dissolve the adhesive without adversely affecting the material itself. One such solvent is THF (tetrahydrofuran, CAS 109-99-9, for general use, available from any convenient source). After the solvent soak, the material layer is allowed to thoroughly air dry in such a way that prevents undue stretching or other deformation of the material. After the material has dried, a test specimen is obtained and tested as per ISO 1833-1 to quantitatively determine its chemical composition.

Fiber Decitex (Dtex)

Textile webs (e.g. woven, nonwoven, airlaid) are comprised of individual fibers of material. Fibers are measured in terms of linear mass density reported in units of decitex. The decitex value is the mass in grams of a fiber present in 10,000 meters of that fiber. The decitex value of the fibers within a web of material is often reported by manufacturers as part of a specification. If the decitex value of the fiber is not known, it can be calculated by measuring the cross-sectional area of the fiber via a suitable microscopy technique such as scanning electron microscopy (SEM), determining the composition of the fiber with suitable techniques such as FT-IR (Fourier Transform Infrared) spectroscopy and/or DSC (Dynamic Scanning Calorimetry), and then using a literature value for density of the composition to calculate the mass in grams of the fiber present in 10,000 meters of the fiber. All testing is performed in a room maintained at a temperature of 23° C.±2.0° C. and a relative humidity of 50%±2% and samples are conditioned under the same environmental conditions for at least 2 hours prior to testing.

If necessary, a representative sample of web material of interest can be excised from an absorbent article. In this case, the web material is removed so as not to stretch, distort, or contaminate the sample.

SEM images are obtained and analyzed as follows to determine the cross-sectional area of a fiber. To analyze the cross section of a sample of web material, a test specimen is prepared as follows. Cut a specimen from the web that is about 1.5 cm (height) by 2.5 cm (length) and free from folds or wrinkles. Submerge the specimen in liquid nitrogen and fracture an edge along the specimen's length with a razor blade (VWR Single Edge Industrial Razor blade No. 9, surgical carbon steel). Sputter coat the specimen with gold and then adhere it to an SEM mount using double-sided conductive tape (Cu, 3M available from electron microscopy sciences). The specimen is oriented such that the cross section is as perpendicular as possible to the detector to minimize any oblique distortion in the measured cross sections. An SEM image is obtained at a resolution sufficient to clearly elucidate the cross sections of the fibers present in the specimen. Fiber cross sections may vary in shape, and some fibers may consist of a plurality of individual filaments. Regardless, the area of each of the fiber cross sections is determined (for example, using diameters for round fibers, major and minor axes for elliptical fibers, and image analysis for more complicated shapes). If fiber cross sections indicate inhomogeneous cross-sectional composition, the area of each recognizable component is recorded and dtex contributions are calculated for each component and subsequently summed. For example, if the fiber is bi-component, the cross-sectional area is measured separately for the core and sheath, and dtex contribution from core and sheath are each calculated and summed. If the fiber is hollow, the cross-sectional area excludes the inner portion of the fiber comprised of air, which does not appreciably contribute to fiber dtex. Altogether, at least 100 such measurements of cross-sectional area are made for each fiber type present in the specimen, and the arithmetic mean of the cross-sectional area $a_k$ for each are recorded in units of micrometers squared (m²) to the nearest 0.1 μm².

Fiber composition is determined using common characterization techniques such as FTIR spectroscopy. For more complicated fiber compositions (such as polypropylene core/polyethylene sheath bi-component fibers), a combination of common techniques (e.g. FTIR spectroscopy and DSC) may be required to fully characterize the fiber composition. Repeat this process for each fiber type present in the web material.

The decitex $d_k$ value for each fiber type in the web material is calculated as follows:

$$d_k = 10\,000\text{ m} \times a_k \times \rho_k \times 10^{-6}$$

where $d_k$ is in units of grams (per calculated 10,000 meter length), $a_k$ is in units of m², and $\rho_k$ is in units of grams per cubic centimeter (g/cm³). Decitex is reported to the nearest 0.1 g (per calculated 10,000 meter length) along with the fiber type (e.g. PP, PET, cellulose, PP/PET bico).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a liquid pervious topsheet, wherein the topsheet comprises a nonwoven, wherein the nonwoven is a through-air bonded nonwoven having a plurality of apertures and a plurality of recessions, wherein the nonwoven comprises hydrophobic fibers and hydrophilic fibers, and wherein the nonwoven comprises at least 50% hydrophilic fibers;
   a backsheet at least peripherally joined to the topsheet;
   an absorbent core disposed between said topsheet and said backsheet;
   an integrated nonwoven fluid management layer having a basis weight between about 40 gsm and about 65 gsm and a caliper factor of greater than 0.2 mm to about 0.3 mm, and wherein the fluid management layer comprises absorbent fibers and stiffening fibers and the ratio of the absorbent fibers to the stiffening fibers is from about 1:7 to about 2:1; and
   a Urine Standard Rewet Value of 10 mg or less.

2. The absorbent article of claim 1 wherein the absorbent article is a liner.

3. The absorbent article of claim 1 wherein the Urine Instant Rewet Value is 4 mg or less, and the absorbent core comprises a basis weight of at least 150 gsm.

4. The absorbent article of claim 1 wherein the topsheet is void of film.

5. The absorbent article of claim 1 wherein the fluid management layer comprises a plurality of resilient fibers.

6. The absorbent article of claim 5 wherein the fluid management layer comprises from about 10% to about 60% by weight of absorbent fibers.

7. The absorbent article of claim 5 wherein the fluid management layer comprises from about 15% to about 70% by weight of resilient fibers.

8. The absorbent article of claim 1 further comprising a Wet CD Bunch Compression of 325 gf or greater.

9. The absorbent article of claim 1 further comprising a Dry CD Bunch Compression Recovery of 50% or greater.

10. A liner comprising:
    a liquid pervious topsheet, wherein the topsheet comprises a nonwoven, wherein the nonwoven comprises hydrophobic fibers and hydrophilic fibers, wherein the nonwoven comprises at least 50% hydrophilic fibers, and wherein the topsheet is void of film;
    a backsheet at least peripherally joined to the topsheet;
    an absorbent core disposed between said topsheet and said backsheet;
    a longitudinal centerline and a transverse centerline;
    an integrated nonwoven fluid management layer having a caliper factor of greater than 0.2 mm to about 0.3 mm, and wherein the fluid management layer comprises absorbent fibers and stiffening fibers and the ratio of the absorbent fibers to the stiffening fibers is from about 1:7 to about 2:1;
    wherein the liner comprises an increasing porosity gradient in a first z direction, wherein the first z direction extends from the backsheet towards the topsheet; and
    a Urine Standard Rewet Value of 10 mg or less,
    wherein the topsheet is from about 5% to about 20% greater in porosity than the fluid management layer.

11. The liner of claim 10 wherein the liner comprises a Wet CD Bunch Compression of at least 325 gf.

12. The liner of claim 10 wherein the fluid management layer is integrated via hydroentangling or needlepunching.

13. The liner of claim 10 wherein the fluid management layer comprise a plurality of resilient fibers.

14. The liner of claim 10 wherein the topsheet comprises a through-air bonded nonwoven having a plurality of apertures and a plurality of recessions.

15. A liner comprising:
    a liquid pervious topsheet, wherein the topsheet comprises a nonwoven, wherein the nonwoven comprises hydrophobic fibers and hydrophilic fibers, wherein the nonwoven comprises at least 50% hydrophilic fibers, wherein the nonwoven comprises a plurality of macro deformations, wherein the plurality of macro deformations comprise a major axis that is greater than about 0.5 mm and less than about 2.0 mm and a minor axis that is greater than 0.4 mm and less than about 1.5 mm, and wherein the topsheet is void of film;

a backsheet at least peripherally joined to the topsheet;

an absorbent core disposed between said topsheet and said backsheet, wherein the absorbent core comprises an airlaid core with a basis weight of at least 150 gsm; and an integrated nonwoven fluid management layer having a basis weight between about 40 gsm and about 65 gsm and a caliper factor of greater than 0.2 mm to about 0.3 mm, and wherein the fluid management layer comprises absorbent fibers and stiffening fibers and the ratio of the absorbent fibers to the stiffening fibers is from about 1:7 to about 2:1;

wherein the liner comprises a Wet CD Bunch Compression of at least 325 gf.

\* \* \* \* \*